(12) United States Patent
Mai et al.

(10) Patent No.: US 12,186,135 B2
(45) Date of Patent: Jan. 7, 2025

(54) REAL-TIME ROBOTIC-ASSISTED DIMENSION MEASUREMENT SYSTEM

(71) Applicant: Verb Surgical Inc., Santa Clara, CA (US)

(72) Inventors: Jianning Mai, Milpitas, CA (US); Wanning Zhu, Sunnyvale, CA (US); Yiming Xu, Sunnyvale, CA (US); Lela DiMonte, Mountain View, CA (US); Mary Lynn Gaddis, Newport Beach, CA (US)

(73) Assignee: Verb Surgical Inc., Santa Clara, CA (US)

( * ) Notice: Subject to any disclaimer, the term of this patent is extended or adjusted under 35 U.S.C. 154(b) by 1017 days.

(21) Appl. No.: 17/030,145

(22) Filed: Sep. 23, 2020

(65) Prior Publication Data
US 2022/0087768 A1 Mar. 24, 2022

(51) Int. Cl.
*A61B 90/00* (2016.01)
*A61B 34/00* (2016.01)
*A61B 34/35* (2016.01)
A61B 34/30 (2016.01)

(52) U.S. Cl.
CPC .............. *A61B 90/06* (2016.02); *A61B 34/25* (2016.02); *A61B 34/35* (2016.02); *A61B 2034/305* (2016.02); *A61B 2090/061* (2016.02)

(58) Field of Classification Search
CPC ......... A61B 90/06; A61B 34/25; A61B 34/35; A61B 2034/305; A61B 2090/061
USPC ............................................................ 606/1
See application file for complete search history.

(56) References Cited

U.S. PATENT DOCUMENTS

| 8,337,397 B2 | 12/2012 | Prisco et al. |
| 9,155,592 B2* | 10/2015 | Itkowitz ................ A61B 34/30 |
| 2003/0195664 A1 | 10/2003 | Nowlin et al. |
| 2014/0055489 A1 | 2/2014 | Itkowitz et al. |

OTHER PUBLICATIONS

Padoy, Nicholas, et al., "Statistical Modeling and Recognition of Surgical Workflow", Medical Image Analysis, Sep. 2010, 22 pages.

* cited by examiner

*Primary Examiner* — Aaron F Roane
(74) *Attorney, Agent, or Firm* — Aikin & Gallant, LLP

(57) ABSTRACT

Disclosed are various real-time robotic-assisted dimension measurement systems and techniques based on the collected kinematic data from one or more surgical tools within a robotic surgical system. In some embodiments, the collected kinematic data can include positions and orientations of each joint of the one or more surgical tools which are derived from positions and orientations of a set of arm joints of one or more robotic arms which the one or more surgical tools are attached to. The disclosed dimension measurement systems allow a surgeon to perform real-time length measurements of both straight-lines and curved-lines, as well as area and volume measurements on specified portions of tissues or organs by strategically placing the tips of the one or more surgical tools over the tissues or organs, while viewing the distal ends of the surgical tools in a user display.

18 Claims, 11 Drawing Sheets

ESTIMATING THE VOLUME OF GASTRIC POUCH 602 USING TWO ROBOTIC TOOLS

REAL-TIME ROBOTIC-ASSISTED DIMENSION MEASUREMENT SYSTEM

TECHNICAL FIELD

The present disclosure generally relates to real-time measurement tools for robotic surgical systems, and more specifically to systems, devices and techniques for performing real-time robotic-assisted dimension measurements of organs and tissues on a robotic surgical system.

BACKGROUND

During robotic surgeries, surgeons may need to measure lengths of tissues or organs in preparation to perform transections or sutures on the tissues or the organs. For example, during a Roux-en-Y gastric bypass (RYGB) procedure, a surgeon may need to perform two length measurements of the patient's intestines. In another example, a surgeon often needs to determine the exposed vaginal length during a vaginal dissection procedure. Traditional tissue or organ length measurements are typically performed using a physical ruler inserted into patient's body and placed in the vicinity of the surgical site. For example, in minimally invasive surgery (MIS), a disposable paper ruler can be delivered into a patient's body through an accessory port and handed off to the surgeon. The surgeon will hold the ruler in front of the target anatomy or defect using one or two surgical instruments for the intended length measurements. After noting the measurements, the surgeon then passes the ruler back to the assistant for removal. However, using a physical ruler for surgical length measurements is intrinsically cumbersome, increases total operation time, and does not apply to certain length measurement situations.

Another common method of length measurement is based on visual estimations. For example, during a Roux-En-Y reconstruction phase of a total gastrectomy procedure, the jejunum is directly connected to the esophagus. In order to choose the starting position of the jejunum, a length of jejunum is typically measured 30~40 cm downstream from the ligament of Treitz. In addition, the surgeon needs to measure another 60~70 cm of jejunum to determine the location to start the jejunojejunostomy. The surgeon must ensure that the selected section of jejunum is sufficiently long to reach the esophagus. To measure these desired lengths of the bowel, the surgeon would visually estimate a distance by counting a number of grasps on the bowel with two surgical instruments using a hand-over-hand technique referred to as "running the bowel." By grasping the bowel with ~5 cm in between the two instruments each time, the surgeon would be able to count the number of grasps and subsequently determine the total length of the bowel traveled between the two instruments. Unfortunately, this visual estimation technique is highly susceptible to the experience level of the surgeon, and is inherently inaccurate.

Hence, it is desirable to provide improved length measurement techniques during robotic surgeries without the above-described problems.

SUMMARY

Described herein are various embodiments of a dimension measurement system for performing real-time robotic-assisted dimension measurements of tissues or organs using one or more surgical tools. In various embodiments, the disclosed dimension measurement system is configured to perform real-time dimension measurements based on the collected robotic log data of one or more surgical tools, wherein the robotic log data can include kinematic data of the one or more surgical tools, including positions and orientations of each joint of the one or more surgical tools.

In one aspect, a process for performing real-time robotic-assisted length measurements within a robotic surgical system is disclosed. This process can begin by obtaining a first set of kinematic data of a wrist joint of a surgical tool corresponding to placing a tool-tip of the surgical tool at a first location on an anatomy, wherein the first set of kinematic data are measured relative to a base reference frame. Next, the process obtains a second set of kinematic data of the wrist joint of the surgical tool corresponding to placing the tool-tip of the surgical tool at a second location on the anatomy, wherein the second set of kinematic data are also measured relative to the base reference frame. The process then transforms the first set of kinematic data into a first position vector of the tool-tip at the first location and the second set of kinematic data into a second position vector of the tool-tip at the second location. The process subsequently computes a first distance between the first position vector and the second position vector as a measured length of a straight line between the first location and the second location on the anatomy.

In some embodiments, prior to obtaining the first set and the second set of kinematic data, the process receives a first user command to initiate a length measurement on the anatomy via a user interface device (UID) of the robotic surgical system.

In some embodiments, after initiating the length measurement, the process further receives a second user command indicative of whether the length measurement is a straight-line measurement or a curved-lined measurement. The process subsequently enters either a straight-line measurement mode or a curved-line measurement mode after processing the second user command.

In some embodiments, the process obtains the first set or the second set of kinematic data of the wrist joint of the surgical tool by: (1) retrieving, from a data log of the robotic surgical system, a position vector corresponding to a center point of the wrist joint; and (2) retrieving, from the data log, a rotation vector corresponding to an orientation of an end effector of the surgical tool connected to the wrist joint. Note that the end effector is positioned between the wrist joint and the tool-tip.

In some embodiments, the process transforms the first set or the second set of kinematic data into the first position vector or the second position vector of the first location or the second location by computing a rotational displacement of the tool-tip with respect to the center point of the wrist joint based at least on the corresponding rotation vector and a length of the end effector. The process subsequently obtains the first position vector or the second position vector of the first location or the second location by combining the first position vector or the second position vector of the center point of the wrist joint with the corresponding rotational displacement.

Note that the surgical tool is attached to a robotic arm comprising a set of arm joints, including a first arm joint and a last arm joint. In some embodiments, the process obtains the first set or the second set of kinematic data of the wrist joint by, for each arm joint in the set of arm joints, obtaining a set of kinematic data generated by an encoder of the arm joint, wherein the set of kinematic data are measured relative to a reference frame of the arm joint. The process then performs a series of forward transformations from the first arm joint to the last arm joint using the sets of kinematic data associated with the set of arm joints. Note that each forward transformation in the series of forward transformations transforms the corresponding set of kinematic data at the corresponding arm joint into a transformed set of kinematic data for the corresponding arm joint relative to the base frame. The process subsequently performs a final forward transformation which transforms the transformed set of kinematic data at the final arm joint into the first set or the second set of kinematic data of the wrist joint of the surgical tool in the base frame.

In some embodiments, after initiating the length measurement, the process can calibrate measurement errors associated with using the tool-tip of the surgical tool with a known length of a second surgical tool of the robotic surgical system. Note that the measurement errors can include an accumulated encoder error associated with the set of encoders of the set of arm joints.

In some embodiments, the process calibrates the measurement errors with the known length of the second surgical tool by: (1) taking multiple length measurements of the known length using the tool-tip of the surgical tool to obtain a set of measurement values of the known length; and then (2) comparing the set of measurement values against the known length to obtain a mean error of the set of measurement values.

In some embodiments, the process takes a length measurement of the known length using the tool-tip of the surgical tool by: obtaining a third position vector of the tool-tip at a first end-point of the known length on the second surgical tool; obtaining a fourth position vector of the tool-tip at a second end-point of the known length on the second surgical tool; and subsequently generating a measurement value of the known length as the distance between the third position vector and the fourth position vector.

In some embodiments, the process uses the calibrated measurement errors to offset the measured length of the straight line to improve a measurement accuracy of using the tool-tip of the surgical tool for length measurements.

In some embodiments, the process further includes steps for measuring a length of a curved line by: (1) obtaining a third set of kinematic data of the wrist joint of the surgical tool corresponding to placing the tool-tip of the surgical tool at a third location on the anatomy, wherein the third set of kinematic data are measured relative to the base reference frame; (2) transforming the third set of kinematic data into a third position vector of the tool-tip at the third location; (3) computing a second distance between the second position vector and the third position vector as a measured length of a straight line between the second location and the third location on the anatomy; and (3) outputting the sum of the first distance and the first distance as an approximated length of a curved line specified by the first, the second and the third locations.

In another aspect, an apparatus for performing real-time robotic-assisted length measurements is disclosed. This apparatus can include one or more processors and a memory coupled to the one or more processors. The memory stores instructions that, when executed by the one or more processors, cause the apparatus to: (1) obtain a first set of kinematic data of a wrist joint of a surgical tool corresponding to placing a tool-tip of the surgical tool at a first location on an anatomy, wherein the first set of kinematic data are measured relative to a base reference frame; (2) obtain a second set of kinematic data of the wrist joint of the surgical tool corresponding to placing the tool-tip of the surgical tool at a second location on the anatomy, wherein the second set of kinematic data are measured relative to the base reference frame; (3) transform the first set of kinematic data into a first position vector of the tool-tip at the first location and the second set of kinematic data into a second position vector of the tool-tip at the second location; and (4) compute a first distance between the first position vector and the second position vector as a measured length of a straight line between the first location and the second location on the anatomy.

In some embodiments, the memory further stores instructions that, when executed by the one or more processors, cause the apparatus to obtain the first set or the second set of kinematic data of the wrist joint of the surgical tool by: (1) retrieving, from a data log of the robotic surgical system, a position vector corresponding to a center point of the wrist joint; and (2) retrieving, from the data log, a rotation vector corresponding to an orientation of an end effector of the surgical tool connected to the wrist joint, wherein the end effector is positioned between the wrist joint and the tool-tip.

In some embodiments, the memory further stores instructions that, when executed by the one or more processors, cause the apparatus to transform the first set or the second set of kinematic data into the first position vector or the second position vector of the first location or the second location by: (1) computing a rotational displacement of the tool-tip with respect to the center point of the wrist joint based at least on the corresponding rotation vector and a length of the end effector; and (2) obtaining the first position vector or the second position vector of the first location or the second location by combining the first position vector or the second position vector of the center point of the wrist joint with the corresponding rotational displacement.

Note that the surgical tool is attached to a robotic arm comprising a set of arm joints, including a first arm joint and a last arm joint. In some embodiments, the memory further stores instructions that, when executed by the one or more processors, cause the apparatus to obtain the first set or the second set of kinematic data of the wrist joint by: (1) for each arm joint in the set of arm joints, obtaining a set of kinematic data generated by an encoder of the arm joint, wherein the set of kinematic data are measured relative to a reference frame of the arm joint; and (2) performing a series of forward transformations from the first arm joint to the last arm joint using the sets of kinematic data associated with the set of arm joints, wherein each forward transformation in the series of forward transformations transforms the corresponding set of kinematic data at the corresponding arm joint into a transformed set of kinematic data for the corresponding arm joint relative to the base frame; and (3) performing a final forward transformation which transforms the transformed set of kinematic data at the final arm joint into the first set or the second set of kinematic data of the wrist joint of the surgical tool in the base frame.

In some embodiments, the memory further stores instructions that, when executed by the one or more processors, cause the apparatus to calibrate measurement errors associated with using the tool-tip of the surgical tool with a known length of a second surgical tool by: (1) taking multiple length measurements of the known length using the tool-tip of the surgical tool to obtain a set of measurement values of the known length; and (2) comparing the set of measurement values against the known length to obtain a mean error of the set of measurement values.

In some embodiments, the memory further stores instructions that, when executed by the one or more processors, cause the apparatus to take a length measurement of the known length by: (1) obtaining a third position vector of the tool-tip at a first end-point of the known length on the second surgical tool; (2) obtaining a fourth position vector of the tool-tip at a second end-point of the known length on the second surgical tool; and (3) generating a measurement value of the known length as the distance between the third position vector and the fourth position vector.

In some embodiments, the memory further stores instructions that, when executed by the one or more processors, cause the apparatus to measure a length of a curved line by: (1) obtaining a third set of kinematic data of the wrist joint of the surgical tool corresponding to placing the tool-tip of the surgical tool at a third location on the anatomy, wherein the third set of kinematic data are measured relative to the base reference frame; (2) transforming the third set of kinematic data into a third position vector of the tool-tip at the third location; (3) computing a second distance between the second position vector and the third position vector as a measured length of a straight line between the second location and the third location on the anatomy; and (4) outputting the sum of the first distance and the first distance as an approximated length of a curved line specified by the first, the second, and the third locations.

In yet another aspect, a robotic surgical system is disclosed. This robotic surgical system can include a robot arm and a surgical tool attached to the robotic arm. The robotic surgical system further includes a computer coupled to the robotic arm and the surgical tool and configured to perform real-time length measurements on an anatomy by: (1) obtaining a first set of kinematic data of a wrist joint of a surgical tool corresponding to placing a tool-tip of the surgical tool at a first location on an anatomy, wherein the first set of kinematic data are measured relative to a base reference frame; (2) obtaining a second set of kinematic data of the wrist joint of the surgical tool corresponding to placing the tool-tip of the surgical tool at a second location on the anatomy, wherein the second set of kinematic data are measured relative to the base reference frame; (3) transforming the first set of kinematic data into a first position vector of the tool-tip at the first location and the second set of kinematic data into a second position vector of the tool-tip at the second location; and (4) computing a first distance between the first position vector and the second position vector as a measured length of a straight line between the first location and the second location on the anatomy.

In some embodiments, the robotic surgical system further includes a user interface device (UID). In some embodiments, prior to obtaining the first set and the second set of kinematic data, the computer of the robotic surgical system is configured to receive a first user command to initiate a length measurement on the anatomy via the UID.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Throughout this patent document, the term "dimension measurement" can refer to all of the following types of measurements: a measurement of a length of a tissue or an organ (also referred to as a "length measurement"), a measurement of an area of a tissue or an organ (also referred to as an "area measurement"), and a measurement of a volume of a tissue or an organ (also referred to as a "volume measurement"). Hence, while some embodiments of the disclosed dimension measurement techniques below are directed to length measurements, the present techniques are not meant to be limited to length measurements.

Surgeons often rely on direct measurements of tissues or organs at the surgical sites for decision making, planning, and sizing. Described herein are various embodiments of a dimension measurement system for performing real-time robotic-assisted dimension measurements, such as length measurements of tissues or organs using one or more surgical tools. In various embodiments, the disclosed dimension measurement system is configured to perform real-time dimension measurements based on the collected robotic log data of one or more surgical tools, wherein the robotic log data can include kinematic data of the one or more surgical tools, including positions and orientations of each joint of the one or more surgical tools.

Figure 1:
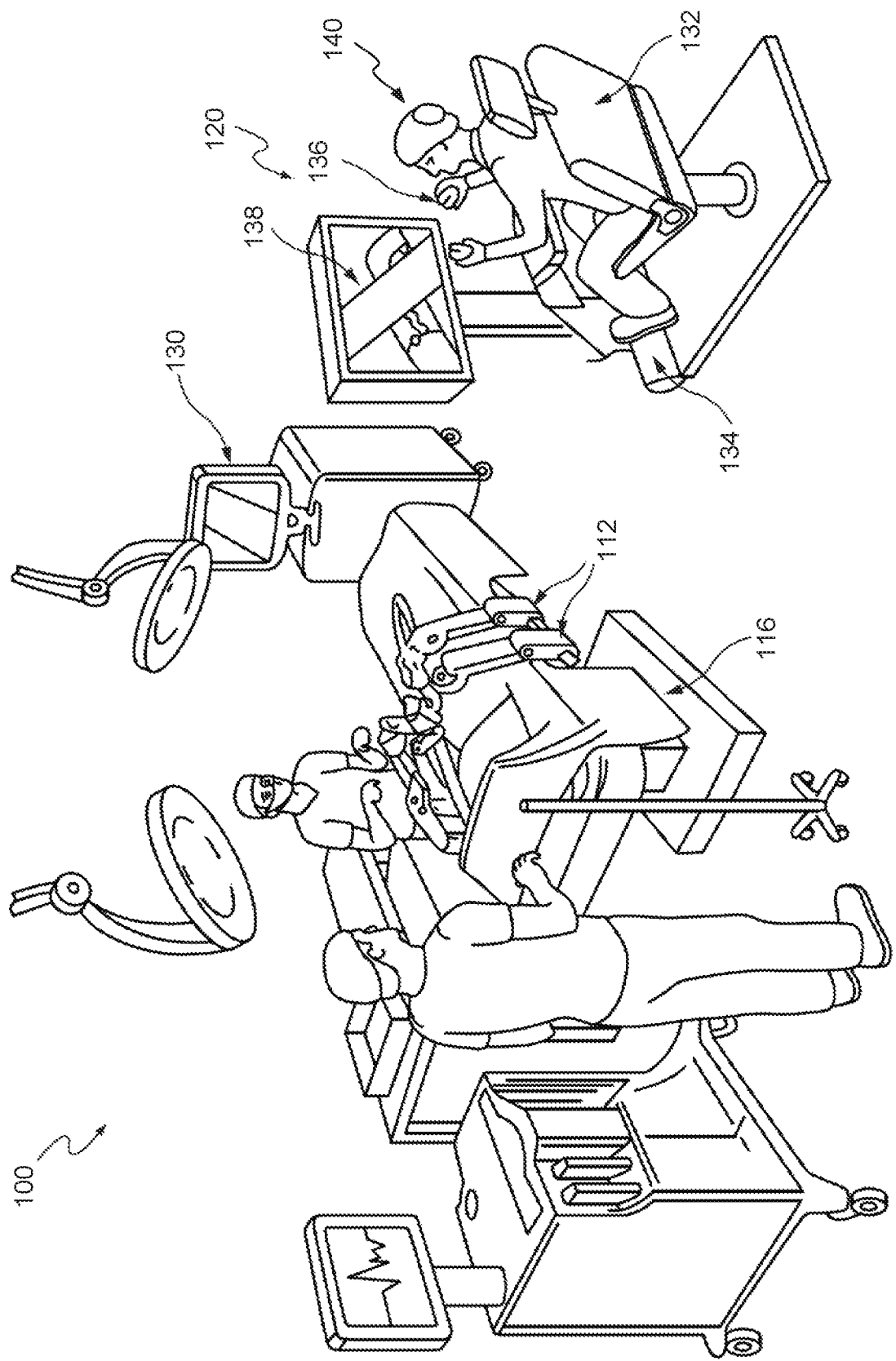
FIG. 1 shows a diagram illustrating an exemplary operating room environment with a robotic surgical system for implementing the disclosed tissue or organ dimension measurement techniques during robotic-assisted surgical procedures in accordance with some embodiments described herein.

FIG. 1 shows a diagram illustrating an exemplary operating room environment with a robotic surgical system 100 for implementing the disclosed tissue or organ dimension measurement techniques during robotic-assisted surgical procedures in accordance with some embodiments described herein. As shown in FIG. 1, robotic surgical system 100 comprises a surgeon console 120, a control tower 130, and one or more surgical robotic arms 112 located at a robotic surgical platform 116 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., teleoperation). User console 120 may be located in the same operating room as robotic surgical system 100, as shown in FIG. 1. In other environments, user console 120 may be located in an adjacent or nearby room, or teleoperated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to achieve anesthesia. Initial access to the surgical site may be performed manually with robotic surgical system 100 in a stowed or withdrawn configuration to facilitate access to the surgical site. Once the access is achieved, initial positioning and/or preparation of the robotic system may be performed. During the procedure, a surgeon in the user console 120 may use the foot-operated controls 134 (e.g., one or more foot pedals) and/or UIDs 136 to manipulate various surgical tools/end effectors and/or imaging systems to perform the surgery. Manual assistance may also be provided at the procedure table by sterile-gowned personnel, who may perform tasks including, but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures including, but not limited to, robotic surgical system 100 cleaning and/or sterilisation, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit them to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

Figure 2:
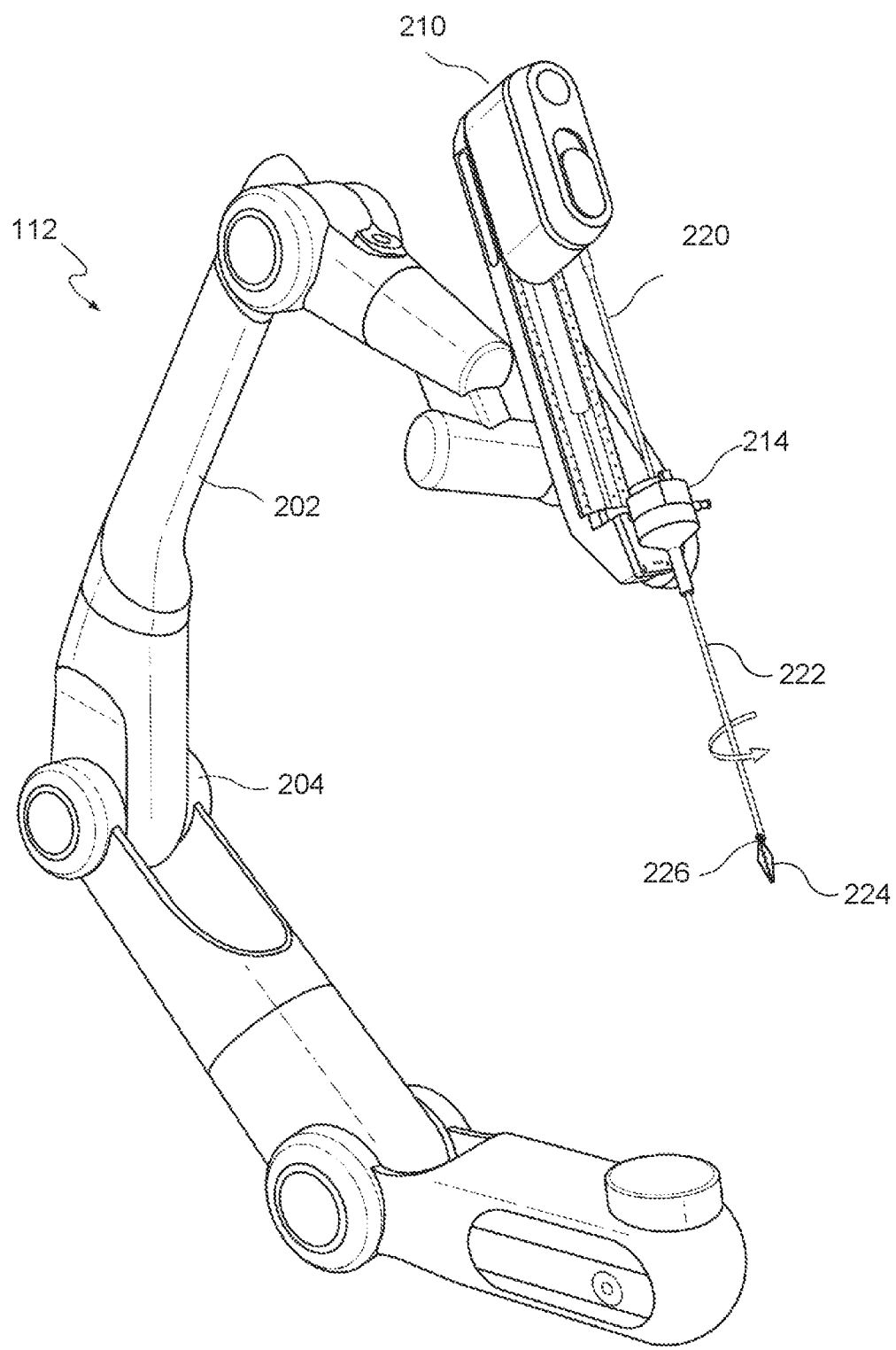
FIG. 2 shows a schematic diagram illustrating an exemplary design of the robotic arm of the robotic surgical system in FIG. 1, which is loaded with a tool drive and a cannula that is further loaded with a robotic surgical instrument, in accordance with some embodiments described herein.

FIG. 2 shows a schematic diagram illustrating an exemplary design of a robotic arm 112 of robotic surgical system 100, which is loaded with a tool drive 210 and a cannula 214 that is further loaded with a robotic surgical instrument 220, in accordance with some embodiments described herein. As shown in FIG. 2, the exemplary surgical robotic arm 112 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others.

Also shown in the exemplary design of FIG. 2 is a tool drive 210 attached to the distal end of the robotic arm 112. The tool drive 210 may include a cannula 214 coupled to its end to receive and guide a robotic surgical instrument 220 (e.g., endoscopes, staplers, graspers, forceps, etc.). This robotic surgical instrument 220 (also referred to as the "robotic surgical tool 220" or the "surgical tool 220" hereinafter) may include a long shaft 222 and an end effector 224 at the distal end of the surgical tool 220. The plurality of the joint modules of the robotic arm 112 can be actuated to position and orient the tool drive 210, which actuates the end effector 222 of the robotic surgical tool 220 for robotic surgeries. Also shown in FIG. 2, shaft 220 and end effector 224 are coupled to each other through a wrist joint 226 (or "joint 226"). End effector 224 can be actuated to rotate in various ways around joint 226. For example, end effector 224 may be actuated to rotate around joint 226 to provide a pitch motion of end effector 224, or a yaw motion of end effector 224, or a combination of both.

Although not explicitly shown, each of the plurality of actuated joint modules, such as joint 204 in robotic arm 112 can include one or more position sensors and one or more rotation sensors (e.g., gyroscopes) for measuring real-time positions and orientations of a respective joint module. As will be discussed in more detail below, the real-time kinematic data including the positions and orientations of each of the plurality of actuated joint modules generated by the integrated position and orientation sensors can be used to determine the real-time positions of wrist joint 226 and the tip of end effector 224 of surgical tool 220.

Real-Time Dimension Measurement System

In this patent disclosure, various robotic-assisted dimension measurement techniques based on the collected robotic log data from one or more robotic surgical tools of the robotic surgical system are disclosure. In various implementations, the collected robotic log data can include kinematic data of certain locations on the one or more surgical tools, including positions and orientations of a wrist joint of a given surgical tool. The disclosed dimension measurement techniques can be used to measure and subsequently generate accurate length, area, and volume values for specified portions of tissues or organs. The disclosed dimension measurement techniques can be implemented within robotic surgical system 100 as part of robotic surgical system 100 to provide real-time tissue/organ length/area/volume measurement solutions. In particular, the disclosed dimension measurement techniques include a robotic-assisted length measurement subsystem (or simply "length measurement subsystem") which be used to generate accurate length/distance values for both straight-lines and curved-lines specified by users on tissues or organs based on the collected robotic kinematic data.

Figure 3:
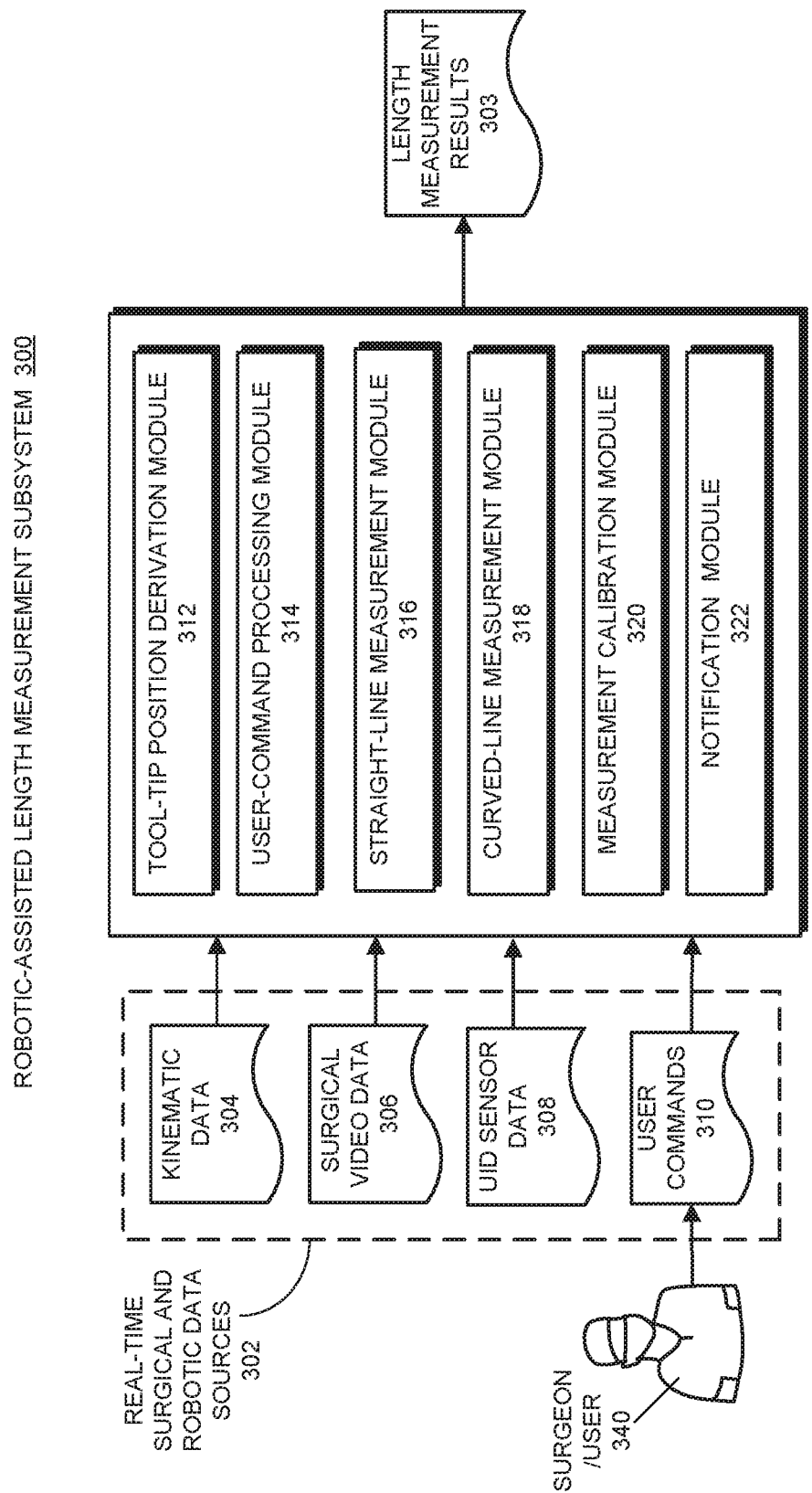
FIG. 3 shows a block diagram of an exemplary robotic-assisted dimension measurement subsystem in accordance with some embodiments described herein.

FIG. 3 shows a block diagram of an exemplary robotic-assisted length measurement subsystem 300 in accordance with some embodiments described herein. As can be seen in FIG. 3, length measurement subsystem 300 can receive a number of real-time surgical and robotic data sources 302 as inputs, process the received robotic data sources 302, and output length measurement results 303 in a three-dimensional (3D) space. More specifically, input data sources 302 can include robot kinematic data 304, surgical video data 306, UID sensor data 308, and user commands 310 such as a length measurement request. As will be described in more detail below, robot kinematic data 304 can include recorded motions of one or two surgical tools, such as the recorded positions and orientations of each tool joint of each surgical tool controlled by a respective robotic arm. Real-time surgical video data 306 can include various types of real-time surgical videos, including but not limited to open surgery videos, endoscopic surgery videos, and robotic surgery videos. UID sensor data 308 can include real-time UID grip force/pressure data for identifying certain types of surgical tool actions and for determining the right timing information (e.g., the proper timestamps) for performing the desired length measurements.

User commands 310 can include various commands issued by a surgeon 340 or a user 340 of robotic surgical system 100 to trigger certain events related to a length measurement. These events can include but are not limited to: initiating a new length measurement; selecting between a straight-line measurement and a curved-line measurement; selecting between a single-tool measurement and a two-tool measurement; and initiating position calculations/derivations for one or more selected point-locations associated with a length measurement. In various embodiments, user commands 310 can include verbal commands, visual commands, gestures, and robotic-commands generated through the one or more UIDs.

As can be seen in FIG. 3, length measurement subsystem 300 can include a number of data-processing modules, each of which can be used to process one or more of the data sources 302 during a disclosed length measurement procedure. More specifically, length measurement subsystem 300 can include a tool-tip position derivation module 312 for processing robot kinematic data 304 and deriving real-time 3D positions of a tool-tip of a surgical tool indicative of one or more point-locations on a measured line. In various embodiments, tool-tip position derivation module 312 is configured to translate the received tool joint positions and orientations data into 3D positions of the tool-tip in a stationary reference frame (e.g., the operating table).

Length measurement system 300 also includes a user-command processing module 314 for processing received user commands 310 and subsequently generating proper control outputs based on the user commands. For example, before starting a new length measurement, user-command processing module 314 can be configured to receive a new user command 310-1 for starting a new length measurement procedure, and initiate the new length measurement in response to user command 310-1. Moreover, after a new length measurement has been initiated, user-command processing module 314 is also configured to receive another user command 310-2 specifying whether a straight-line measurement or a curved-line measurement is to be performed. User-command processing module 314 subsequently causes length measurement subsystem 300 to enter either a straight-line measurement mode or a curved-line measurement mode based on user command 310-2. In some embodiments, after entering the straight-line measurement mode, user-command processing module 314 is further configured to receive another user command 310-3 specifying whether a single-tool measurement or two-tool measurement is to be performed. User-command processing module 314 subsequently causes length measurement system 300 to enter either a single-tool measurement mode or a two-tool measurement mode based on user command 310-3. Note that user-command processing module 314 can be engaged multiple times throughout a length measurement procedure.

Length measurement subsystem 300 can also include a straight-line measurement module 316 for determining a straight line distance between two marked or otherwise specified tool-tip positions and a curved-line measurement module 318 for determining the total length of a trajectory between a starting point and an end point traversed by a single tool-tip. In some embodiments, straight-line measurement module 316 and curved-line measurement module 318 can be integrated as a single length measurement module. Note that straight-line measurement module 316 can also be configured as a component of curved-line measurement module 318 because curved-line measurement module 318 can use straight-line measurement module 316 to calculate the length of each straight-line segment of multiple straight-line segments that the curve line is composed of. Moreover, each of straight-line measurement module 316 and curved-line measurement module 318 can be configured to use tool-tip position derivation module 312 multiple times to derive real-time 3D positions of one or more tool-tips during either a straight-line measurement or a curved-line measurement. Hence, in some embodiments, tool-tip position derivation module 312 can be integrated into both straight-line measurement module 316 and curved-line measurement module 318.

Length measurement subsystem 300 can further include a length calibration module 320 for calibrating length measurement errors associated with tool-tip position derivation module 312, straight-line measurement module 316, and curved-line measurement module 318. As will be discussed below, length measurement errors of length measurement subsystem 300 can include encoder errors originated from the encoders in robotic arms 112 which control the motions of the one or two surgical tools used in the length measurements, as well as encoder errors associated with one or more tool joints of the one or two surgical tools. Hence, measurement calibration module 320 can be used to determine robotic-arm and/or tool encoder errors as well as other types of systematic measurement errors associated with the disclosed length measurement subsystem 300. Furthermore, measurement calibration module 320 can be configured to offset/correct or otherwise mitigate various measurement errors from the length measurement outputs 330 based on the error calibration results.

Length measurement subsystem 300 can also include a notification module 322 for generating and displaying length measurement results 303 to the surgeon/user 340 after performing a new length measurement, thereby providing real-time feedback, assistance, and/or guidance to the surgeon/user performing a surgical or training procedure. For example, notification module 322 can cause the calculated and estimated length values to be displayed on the user console and/or directly announce to the user with an audio. We now describe various implementations of tool-tip position derivation module 312, straight-line measurement module 316, curved-line measurement module 318, and measurement calibration module 320 in more detail.

Tool-Tip Position Derivation

In various embodiments, the disclosed length measurement subsystem 300 can perform tissue/organ length measurements by using the distal ends of one or more robotic surgical tools visible in the user display 138 during teleoperations. In some embodiments, the tips (or "tool-tips") of two surgical tools can be used simultaneously to mark two locations on a tissue/organ, and the disclosed length measurement subsystem 300 is configured to determine the distance between the two marked locations once a length measurement command is received. Alternatively in some other embodiments, the tool-tip of a single surgical tool can be used to sequentially mark two locations on a tissue/organ, and the disclosed length measurement system 300 is configured to determine the distance between the two sequentially marked locations in the 3D space. In these embodiments, the disclosed length measurement subsystem 300 is configured to perform two separate measurements of the tool-tip positions in the 3D space, and subsequently calculate the distance between the two determined tool-tip positions. In addition to performing straight line distance measurements, disclosed length measurement subsystem 300 can also be configured to measure or approximate the length of a curved line. In these embodiments, the tool-tip of a single surgical tool can be used to sequentially mark a series of point-locations of short intervals along a desired curve for measurement on a tissue/organ, and the disclosed length measurement subsystem is configured to determine each straight line distance between each pair of adjacent marked points in the series of points, and subsequently determine the length of the curve by summing up the set of short distances. As mentioned above, length measurement subsystem 300 can also be used to measure areas and volumes of organs/tissues based on measuring lengths and distances in multiple dimensions on the organs/tissues.

Note that for each of the disclosed length, area and volume measurement techniques, the building blocks of each dimension measurement are the positions of the tool-tips which are used to mark/specify a starting point and an end point in straight-line measurements or a set of points in curved-line measurements. However, the positions of these measurement points are not directly available because there are typically no position sensors placed at the tool-tips. Using robotic arm 112 in FIG. 2 as an example, note that the pose, i.e., the 3D positions of the apex/tip of end effector 224 are not directly available.

However, in the example of FIG. 2, the kinematic data are generally available at each joint of the robotic arm 112 through the corresponding encoders. Moreover, kinematic data can also be obtained for a given joint in surgical tool 220, such as the wrist joint and the jaw joint of the surgical tool, through the corresponding actuation mechanism and encoders. In some embodiments, to obtain the kinematic data for the final joint 226 on surgical tool 220, a series of forward transformations can be performed starting from an origin (e.g., origin 212) in a stationary reference frame (also referred to as the "base frame," more about this later in reference to FIG. 4). First, the kinematic data of the very first joint 228 relative to origin 212 will be determined based on the encoder data collected for joint 228. Next, the kinematic data of the second joint 204 relative to origin 212 will be determined based on the computed kinematic data for joint 228 and the encoder data collected for joint 204. These forward transformations continue until the kinematic data of wrist joint 226 of end effector 224 relative to origin 212 can be obtained.

In some embodiments, during a disclosed length measurement, the disclosed length measurement subsystem 300 is configured to collect encoder data (including positions and orientations) for all joints in robotic arm 112 and each tool joint in surgical tool 220, and subsequently generate the pose (i.e., the kinematic data) of wrist joint 226 of end effector 224 relative to the stationary reference frame. However, for the proposed length measurements, it is still necessary to determine the 3D pose/position at the apex/tip of end effector 224.

Figure 4:
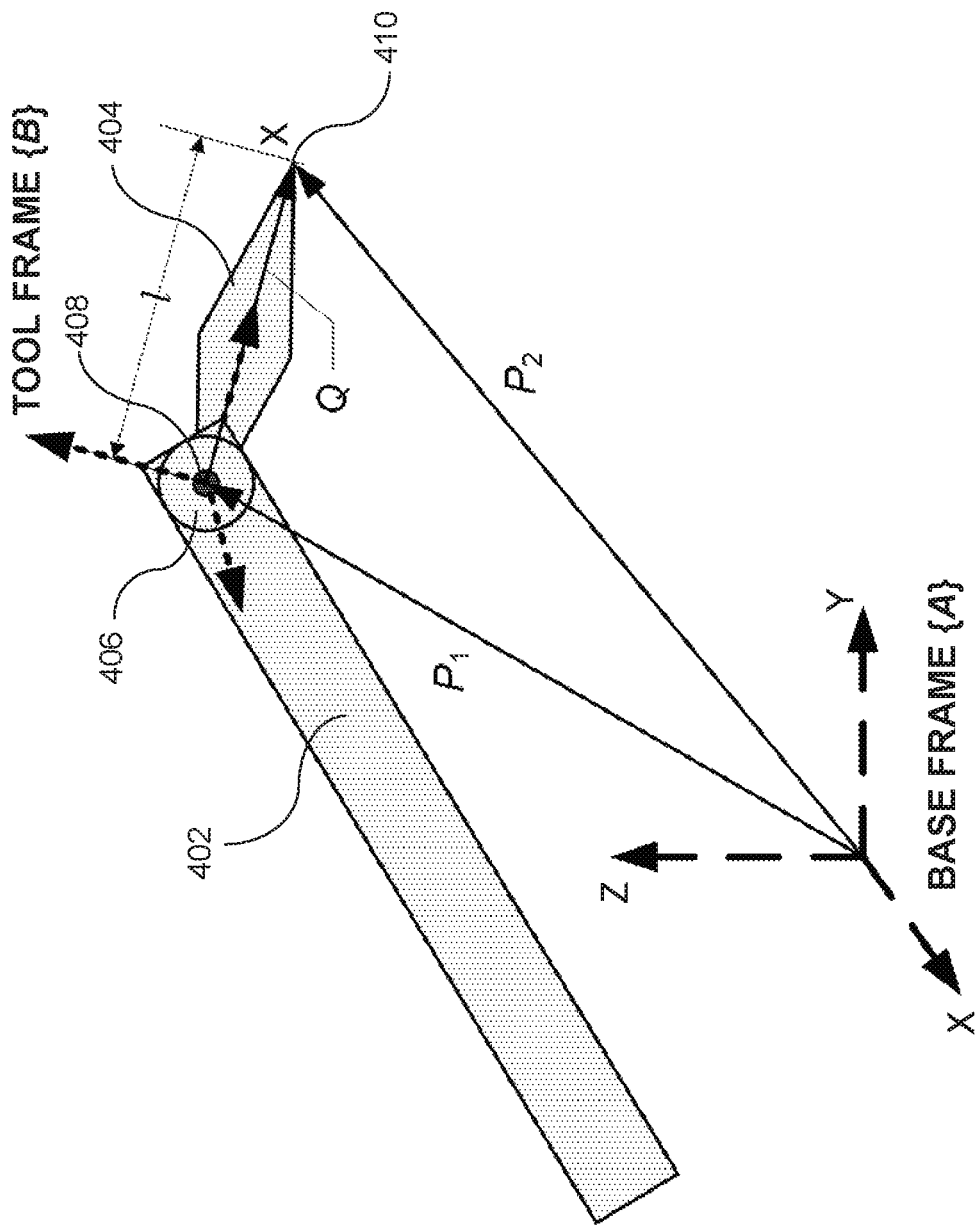
FIG. 4 illustrates a schematic representation of a surgical tool attached to a robotic arm (not shown) and a technique for determining three-dimensional (3D) positions of the tip of surgical tool 400 in accordance with some embodiments described herein.

FIG. 4 illustrates a schematic representation of a surgical tool 400 attached to a robotic arm 112 (not shown) and a technique for deriving/determining 3D positions of the tip of surgical tool 400 in accordance with some embodiments described herein. As can be seen in FIG. 4, the distal end of surgical tool 400 includes a portion of the frame (or the "shaft") 402 and an end effector 404 (configured in the form of a pair of jaws), which are connected to each other through a joint 406 (also referred to as the "wrist joint" of tool 400). Note that this illustrated portion of surgical tool 400 is usually visible to surgeons in the user display 138 during teleoperations. As mentioned above, the pose of joint 406, and in particular of center point 408 of joint 406 in its own reference frame can be collected by surgical system 100, and the pose of joint 406 relative to the origin can determined/derived based on the aforementioned forward transformations. However, the disclosed length measurement techniques are based on the 3D positions of two end points of a straight line marked by the apex, i.e., tool-tip 410 of end effector 404, which cannot be directly measured or obtained.

In some embodiments, the disclosed length measurement subsystem 300 can use tool-tip position derivation module 312 to process the available kinematic data associated with joint 406 and derive the 3D positions of tool-tip 410 for each placement of tool-tip 410 during a given length measurement. From FIG. 4, a number of observations can be made: (1) when center point 408 of joint 406 moves relative to a stationary reference frame, tool-tip 410 moves the same amount relative to the stationary reference frame as a result of the mechanical attachment between joint 406 and tool-tip 410; and (2) tool-tip 410 can rotate around center point 408 to cause additional displacement of tool-tip 410, and the additional displacement caused by this rotational motion depends on the length l of end effector 404 and the amount of rotation (i.e., the angle of rotation). Hence, the positions of tool-tip 410 can be determined as a combination of the known positions of center point 408 and an additional amount of displacement of tool-tip 410 relative to joint 406 (or more specifically to center point 408) as a result of a specific amount of rotation of end effector 404 around center point 408.

In some embodiments, the collected kinematic data associated with joint 406 include two components: the positions of center point 408 and orientations of center point 408, both are relative to a base frame $\{A\}$, which is a global frame of reference. For example, base frame $\{A\}$ can be that of the robotic surgical platform 116, e.g., the surgical table or the endoscope. As mentioned above, the positions and orientations of center point 408 can be derived through forward transformation. In some embodiments, to describe the orientations of center point 408, we first define a tool frame of reference $\{B\}$ (or simply "tool frame $\{B\}$"). As shown in FIG. 4, the x-axis of tool frame $\{B\}$ is defined such that it is aligned with a line connecting center point 408 and tool-tip 410, and as such tool frame $\{B\}$ rotates in tandem with the rotation of end effector 404 around center point 408. In some embodiments, the orientations of center point 408, i.e., the orientations of the end effector 404 relative to base frame $\{A\}$ can be expressed in quaternions $(q_x, q_y, q_z, q_w)$. Although the following discussion to derive the tool-tip positions is based on the quaternions representation, other embodiments can use other equivalent systems to represent the orientations/rotations instead of using the quaternions.

Note that the movement of tool-tip 410 of end effector 404 can include two components: (1) a translational motion in tandem with center point 408; and (2) a rotational motion around center point 408. Hence, the positions of tool-tip 410 as a result of the translational motion can be derived simply as a linear transformation of derived Cartesian positions $(x_1, y_1, z_1)$ of center point 408. In some embodiments, the additional position changes of tool-tip 410 due to the rotational motion can be derived based on the derived orientations $(q_x, q_y, q_z, q_w)$ and the geometries of end effector 404.

More specifically, because tool-tip 410 is located on the x-axis of tool frame $\{B\}$ and the origin of tool frame $\{B\}$ coincides with center point 408, the positions of tool-tip 410 in tool frame $\{B\}$ can be expressed as $^B Q=(l, 0, 0)$, wherein l is the distance between center point 408 and tool-tip 410, or approximately the length of end effector 404. Because the quaternions $(q_x, q_y, q_z, q_w)$ represent the amount rotations of the tool frame $\{B\}$/end effector 404 relative to base frame $\{A\}$, we can derive a rotation matrix R of the tool frame $\{B\}$ relative to the base frame $\{A\}$ based on the quaternions as follows:

$$R = \begin{bmatrix} q_w^2 + q_x^2 - q_y^2 - q_z^2 & 2q_x q_y - 2q_w q_z & 2q_x q_z + 2q_w q_y \\ 2q_x q_y + 2q_w q_z & q_w^2 - q_x^2 + q_y^2 - q_z^2 & 2q_y q_z - 2q_w q_z \\ 2q_x q_z - 2q_w q_y & 2q_y q_z + 2q_w q_x & q_w^2 - q_x^2 - q_y^2 + q_z^2 \end{bmatrix}. \quad \text{Eqn. 1}$$

Based on the above information, the 3D-position vector of tool-tip 410 in the base frame $\{A\}$, $^A P_2$ can be derived as follows:

$$^A P_2 = R \cdot ^B Q + ^A P_1 \quad \text{Eqn. 2}$$

wherein $^A P_1$ is the position vector of center point 408 (i.e., the derived positions $(x_1, y_1, z_1)$) of center point 408, and $R \cdot ^B Q$ is the additional positional changes of tool-tip 410 due to an amount rotation around center point 408.

Note that the above-described tool-tip position derivation technique associated with Eqn. 2 can be implemented in tool-tip position derivation module 312 for deriving the 3D positions of tool-tip 410 relative to base frame $\{A\}$ at each moment in time. Using this tool-tip position derivation technique, each time tool-tip 410 marks or points to a new location (i.e., by touching) on a tissue or an organ, the disclosed length measurement subsystem 300 can apply the technique to determine the current Cartesian positions (x, y, z) of tool-tip 410. Because these marked/specified locations by the tool-tip(s) are the building blocks of each length, area, and volume measure, the disclosed tool-tip position derivation technique can be repeatedly applied to all marked/specified locations by one or two surgical tools to obtain the corresponding 3D positions of the corresponding tool-tip(s) in base frame $\{A\}$. Also note that while the above technique is described in the scope of using the most distal joint of the surgical tool as the reference point, the disclosed tool-tip position derivation technique is not limited to the most distal joint of the surgical tool. For example, if the surgical tool includes more than one wrist joint, any one of these wrist joints may be used as the reference point for the tool-tip position calculations, provided that the position and orientation data can be collected for the selected joint.

Real-Time Length Measurements

The disclosed length measurement subsystem 300 allows for measuring lengths of both straight-lines and curved-lines over tissues or organs with the assistants of the distal ends of one or two surgical tools controlled by a surgeon using one or two corresponding UIDs while viewing the distal ends of the surgical tools in the user display 138. In some embodiments, the disclosed length measurement subsystem 300 can automatically determine whether to measure a straight-line distance or a curved-line length (e.g., based on analyzing the tool-tip movements), and subsequently apply a corresponding measurement procedure based on the determinations. In some other embodiments, prior to performing a new length measurement, the disclosed system can directly receive a user command specifying whether a straight-line measurement or a curved-line measurement is to be performed. For example, the user command specifying if a surgeon would like to measure the length of a straight line or a curve can be issued by the surgeon as a voice command or via one of two predefined gestures. Subsequently, the disclosed length measurement subsystem translates the user command into either a straight-line decision or a curved-line decision and selects either the straight-line measurement mode or the curved-line measurement mode accordingly.

If the disclosed length measurement subsystem 300 enters the straight-line measurement mode, the system awaits to receive commands to measure the positions of the two end-points of a desired straight-line on a tissue or an organ. More specifically, to measure a straight-line, the surgeon can mark the two end-points of the straight-line using one or two surgical tools currently engaged and manipulated by the surgeon. When a single surgical tool is used, the surgeon can use the tool-tip of the single tool to sequentially mark two locations on a tissue/organ, representing the two end-points of a desired straight-line. Each time the tool-tip is temporarily stopped/positioned at one of the two desired locations, the surgeon can issue a measurement request/command (e.g., double-pinching a corresponding UID, double-tapping a foot pedal, or a combination of using the UID and the foot pedal) to cause a position measurement to be taken instantly or with minimum delay for the current location of the tool-tip. As described above, taking the tool-tip position measurement can include deriving the real-time positions and orientations of a tool joint on the single tool and subsequently deriving the 3D positions of the tool-tip of the single tool in a base frame using the above-described tool-tip position derivation technique. Once the 3D positions of the two end-points in the base frame are determined (e.g., as $P_1(x_1, y_1, z_1)$ and $P_2(x_2, y_2, z_2)$), the disclosed length measurement subsystem 300 can obtain the straight-line distance between the two marked locations (e.g., as $\sqrt{(x_2-x_1)^2+(y_2-y_1)^2+(z_2-z_1)^2}$).

Alternatively, surgeon can use two tool-tips of two surgical tools together and simultaneously mark or point at two locations on a tissue/organ, representing the two end-points of a desired straight-line. After the two tool-tips are positioned at the two desired locations, the surgeon can issue a measurement command (e.g., double-pinching a UID, double-tapping a foot pedal, or a combination of using the UID and the foot pedal) to cause two position measurements to be taken instantly or with minimum delay for the two current locations of both tool-tips. Note that taking two concurrent measurements of two tool-tips can include deriving the real-time positions and orientations of the two corresponding tool joints on the two surgical tools and subsequently deriving the 3D position vectors of both tool-tips in a base frame using the above-described tool-tip position derivation technique. Once the positions of the two end-points in the base frame are determined (e.g., as $P_1(x_1, y_1, z_1)$ and $P_2(x_2, y_2, z_2)$), the disclosed length measurement subsystem obtains the straight-line distance between the two marked locations.

In some embodiments, after entering the straight-line measurement mode, the disclosed length measurement subsystem 300 is also configured to allow the surgeon to choose one of the single-tool and two-tool measurement options based on using two different types of user commands to distinguish between these two options. For example, the system can be configured to trigger a single position measurement upon receiving a user command in the form of a single-pinch of a UID, and to trigger two concurrent position measurements upon receiving a user command in the form of a double-pinch of a UID. Note that the various straight-line measurement techniques described above can be implemented within straight-line measurement module 316 of the disclosed length measurement subsystem 300.

In addition to performing straight-line distance measurements, the disclosed length measurement subsystem 300 is also configured to measure the length along a curved line. If the disclosed length measurement subsystem 300 enters the curved-line measurement mode, the system awaits to receive commands to measure positions of multiple point-locations along a desired curve. In some embodiments, to initiate a curved-line measurement on a tissue/organ, the tool-tip of a single surgical tool is preferably used to swipe along an intended trajectory between a starting point and an end-point on the tissue/organ to trace out the desired curved line. As the surgeon is guiding the tool-tip along the curved-line between the starting and end points, multiple point-locations (or simply "points") along the tool-tip trajectory can be marked/specified for real-time or subsequent estimate of the curved-line length.

For example, a surgeon can double-tap the controlling UID a number of times as he/she is "drawing" the desired curve with the tool-tip (including the starting and end points) to specify a series of points for position measurements. For each marked/specified point in the series of points, the disclosed length measurement subsystem 300 is configured to determine the 3D positions of the marked/specified point in the base frame using the above-described tool-tip position derivation technique. After the 3D positions of the series of points along the curved-line have been derived, the disclosed length measurement subsystem 300 subsequently calculates the length of a line segment between each pair of neighboring points in the series of points. Finally, the disclosed length measurement subsystem 300 can calculate an approximated length of the user-specified curve by summing up all of the calculated lengths of the set of line segments. Note that the various curved-line measurement techniques described above can be implemented within curved-line measurement module 318 of the disclosed length measurement subsystem 300.

After a user-requested length measurement (either for a straight-line or a curved-line) has been performed, the disclosed length measurement subsystem 300 is configured to provide real-time feedback to the user. For example, the disclosed length measurement subsystem 300 can cause the calculated length for a straight-line or the estimated length for a curved-line to be displayed in user display 138 and/or announced to the user by voice/audio to provide the surgeon with real-time feedback, assistance, and/or guidance. Note that the various real-time measurement feedback functions can be implemented with notification module 322 of the disclosed length measurement subsystem 300.

Length Measurement Calibration and Error Mitigation

The above-described length measurement techniques rely on the derived kinematic (including positions and orientations) data at tool joints, which themselves can include various types of errors. Such errors are then propagated into the derived length values generated by length measurement subsystem 300. As such, it is necessary to determine/calibrate systematic errors associated with length measurement subsystem 300 and use error calibration results to correct/offset the length measurement values generated by length measurement subsystem 300.

In the tool-tip position derivation procedure described above, we noted that the geometries of the distal end of surgical tool 400, such as length l of end effector 404 can have known length values. It is also noted that length l is not necessarily a fixed value but a value that depends on the model and type of exemplary robotic tool 400. However, because surgical tools of the same type and model are generally designed and manufactured with certain standard dimensions and geometries, a specific part of a surgical tool, such as length l of end effector 404 of a specific type and model should be a constant value, referred to as the "reference length." In some embodiments, this reference length can be used in a length measurement calibration procedure to determine the systematic errors associated with the disclosed length measurement subsystem 300. Hence, depending on what type and model of a robotic tool is actually used in the length measurement and length measurement calibration procedures, the reference length used by the disclosed length measurement calibration procedure can have different values.

Figure 5:
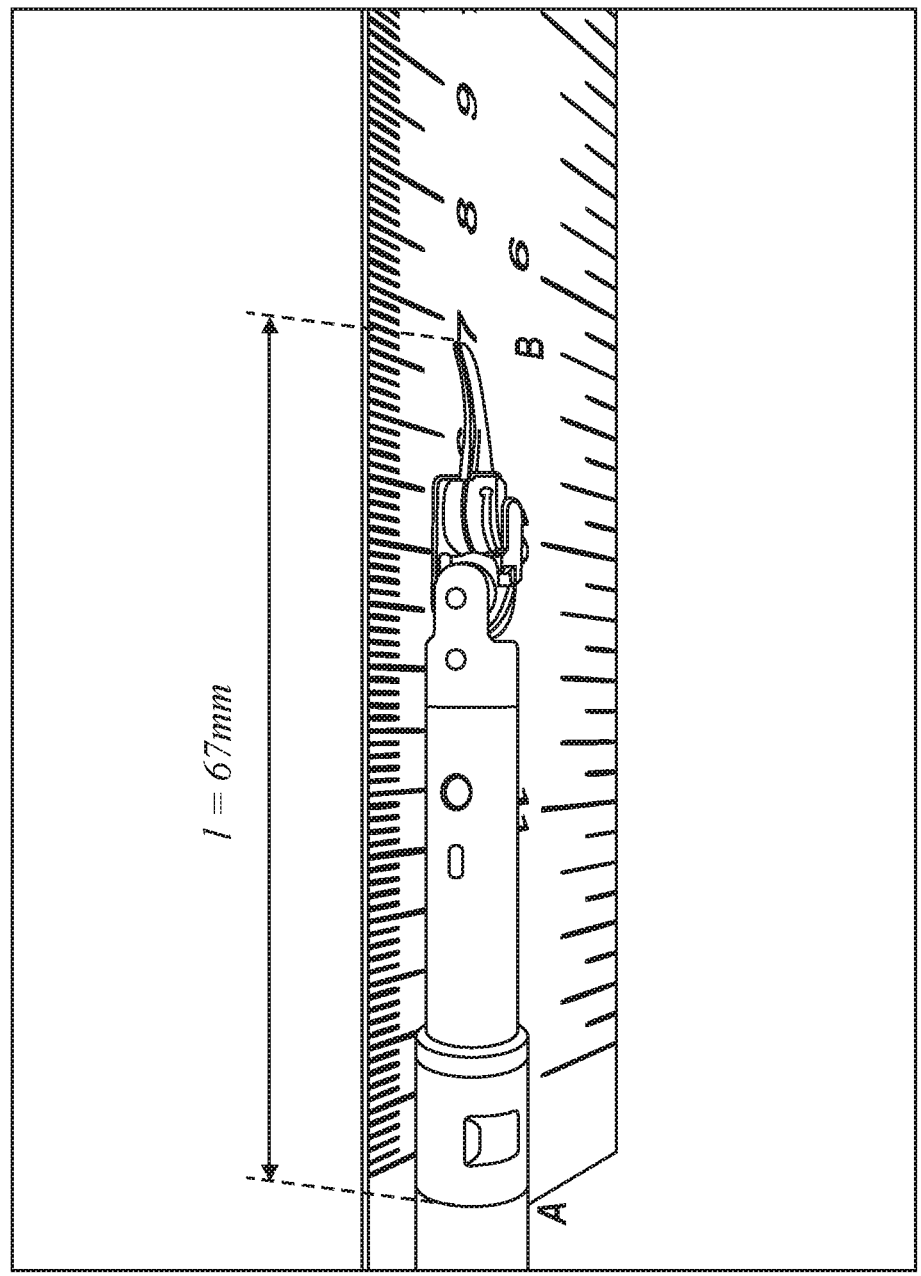
FIG. 5 shows the distal end of a pair of monopolar curved scissors (MCS) used to provide a reference length in a length measurement calibration procedure in accordance with some embodiments described herein.

For example, FIG. 5 shows the distal end of a pair of monopolar curved scissors (MCS) 500 used to provide a reference length in a length measurement calibration procedure in accordance with some embodiments described herein. As can be seen in FIG. 5, the distal end of MCS 500 can include a portion of the shaft, one or more wrist joints, and the end effector. For MCS 500, length l between a reference point A (i.e., the starting point of the chrome shaft part) and the tool-tip B has an approximately length of 67 mm. Hence, when MCS 500 is used in the disclosed length measurement procedures, the known length l can be used as the reference length for length measurement calibration prior to performing the actual length measurements.

In some embodiments, calibrating the length measurements involves taking one or multiple measurements of the known length AB between point A and tool-tip B using the disclosed length measurement techniques (e.g., by placing a tool-tip at point A and point B respectively and engaging length measurement subsystem 300 twice to take two position measurements). As described above, each calibration measurement can be performed with a single surgical tool by taking two separate position measurements or with two surgical tools by taking two simultaneous position measurements. In some embodiments, the calibration measurements can be performed using only one surgical tool if the surgeon is to perform the subsequent length measurements also with just one surgical tool. Alternatively, the calibration measurements can be performed using two surgical tools if the surgeon is to perform the subsequent length measurements with two surgical tools.

Regardless of whether a single-tool or a two-tool length calibration is performed, the disclosed measurement calibration technique can determine a mean error MAE of the multiple calibration measurements by comparing the multiple length measurement values for length AB using the disclosed length measurement techniques against the known length AB. The mean error MAE can then be used to correct/offset actual length measurement values generated by the disclosed length measurement techniques.

As mentioned above, tools of different types and models can have different reference lengths between a corresponding point A and a corresponding tool-tip B. Robotic surgical system 100 can include a mechanism to obtain and provide proper reference lengths during various length measurement calibration procedures based on specific tool IDs and/or tool types of the tools used as the reference lengths. In some embodiments, the reference length information of a surgical tool can be obtained by robotic surgical system 100 at the moment when the tool is attached to a robotic arm 112 and subsequently provided to the disclosed length measurement subsystem 300 as the reference length in a measurement calibration procedure when the tool remains attached.

Also described above, systematic errors when using the disclosed length measurement techniques can come from the collected tool kinematic data at the last tool joint because these data are derived from multiple encoders at multiple robotic arm joints and tool joints. As such, systematic errors include encoder errors accumulated at each of the multiple joints along the robotic arm the surgical tool. Sometimes such errors can amount to around 10%. It can be appreciated that a predicted length value between two tool-tips in a two-tool measurement procedure can have even bigger errors as a result of the encoder errors associated with both robot arms and relative errors between the two surgical tools, which can add up to 20%. In some embodiments, to reduce encoder errors, length measurement calibrations can be performed for each of the two robotic arms separately (i.e., to determine the errors for the disclosed single-tool length measurement option) and also for distances measured using both robotic arms (i.e., to determine the errors for the disclosed two-tool length measurement option). Note that these encoder error calibrations can be performed in real-time prior to a length measurement procedure as described above or performed separately offline.

In another measurement calibration technique, instead of using the aforementioned reference length and comparing to measured lengths, the tool-tip positions can be measured using an independent tracking device having high measurement precisions (e.g., using an optical tracking system) under various poses and configurations of each robotic arm 112. Next, the tool-tips positions measured by the high-precision tracking device can be compared to the tool-tips positions generated by the disclosed length measurement subsystem 300 to determine a mean error value for tool-tip position measurements. Subsequently during a length measurement using the disclosed length measurement subsystem 300, the determined mean error value for a given robotic arms 112 can be used to offset the encoder errors in the position estimations by a single tool using the disclosed length measurement technique.

Note that a similar measurement calibration technique can be applied to the distance measurements between two tool-tips attached to two robotic arms 112. More specifically, the high-precision track device can be used to directly measure distances between the two tool-tips under various tool-tips placements. Next, the distances measured by the tracking device are compared to the corresponding distance measurements generated by the disclosed length measurement subsystem 300 to determine a mean error value. Subsequently during a length measurement using the disclosed length measurement subsystem 300, the determined mean error value for two robotic arms 112 used together can be used to offset the encoder errors in the length estimations when two-tool measurement option is selected. Note that other than the physical devices, the various disclosed length measurement calibration techniques and various error correction/offset/mitigation procedures can be implemented on measurement calibration module 320 of the disclosed length measurement subsystem 300.

Note that the above-described length measurement subsystem 300 and the length measurement calibration techniques can be easily extended to measure areas and volumes and to calibrate such measurement results of specified portions of tissues or organs. Hence, the disclosed length measurement subsystem 300 and the disclosed length measurement calibration techniques are not limited to length measurements.

Real-Time Dimension Measurement Applications

Figure 6:
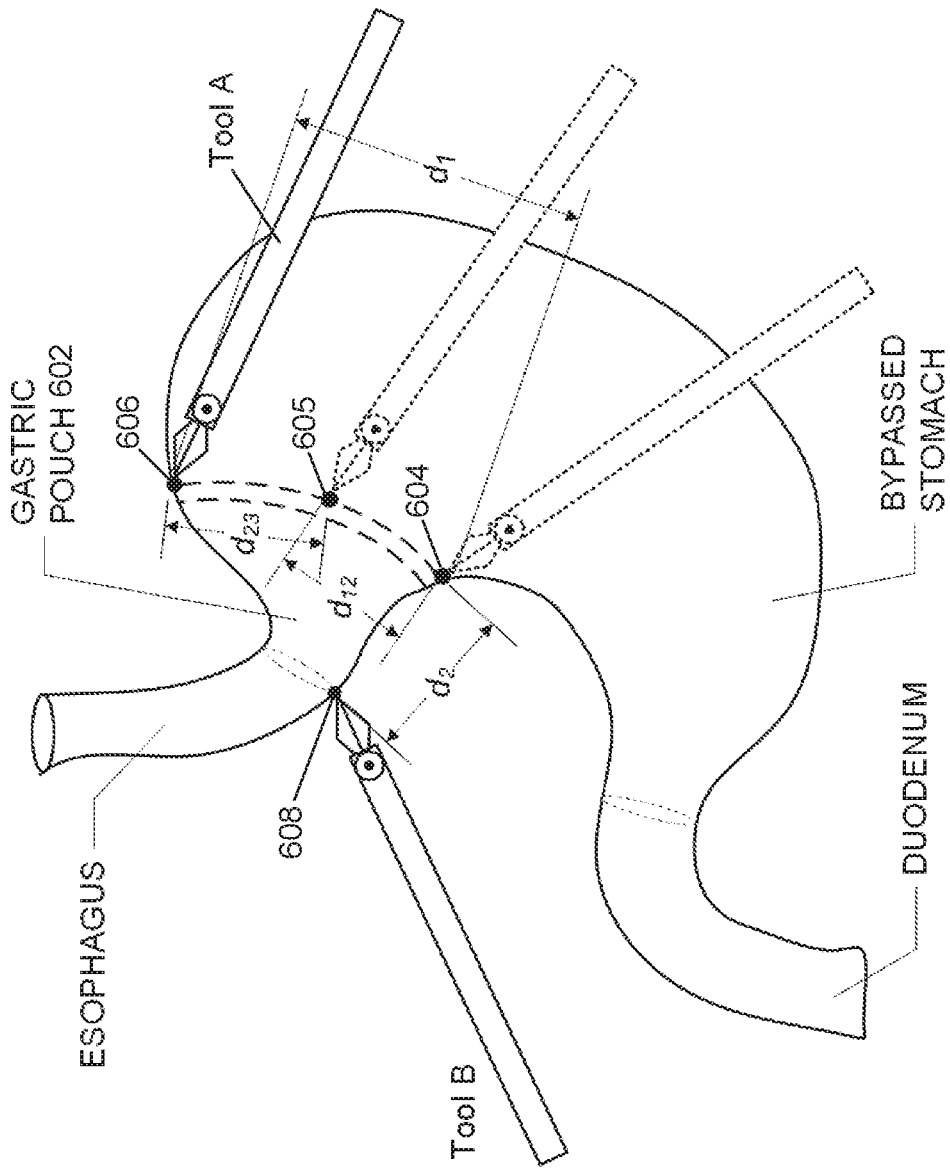
FIG. 6 illustrates using the disclosed length measurement techniques to estimate various geometries including the volume of a gastric pouch during a Roux-en-Y gastric bypass (RYGB) surgery in accordance with some embodiments described herein.

FIG. 6 illustrates using the disclosed length measurement techniques to estimate various geometries including the volume of a gastric pouch during a Roux-en-Y gastric bypass (RYGB) surgery in accordance with some embodiments described herein. As can be seen in FIG. 6, during the RYGB surgery, a surgeon is intended to create a small gastric pouch 602 having an approximated size of an egg by separating a small section of the stomach away from the rest of the stomach. For example, gastric pouch 602 can be constructed by cutting the main stomach along a curve comprising two curved-lines connecting points (604, 605) and (605, 606) respectively in FIG. 6. In order to estimate the length of the curve between 604 and 606 and/or the volume of the gastric pouch 602, the surgeon can first initiate the length measurement mode with a gesture, such as by swiping surgical tool A along the intended cut line from starting point 604, through point 605, to end point 606, and at each of the three points, triggering a position measurement task with a predetermined gesture such as a double-grip on the UID controlling tool A. Following each measurement command, the disclosed length measurement subsystem 300 can be engaged to generate a derived position vector for each of the three points 604, 605, and 606. Assuming the derived position vectors of points 604, 605, 606 are $P_1$, $P_2$, and $P_3$, wherein:

$$P_1 = (x_1, y_1, z_1), \quad \text{Eqn. 3}$$

$$P_2 = (x_2, y_2, z_2), \quad \text{Eqn. 4}$$

$$P_3 = (x_3, y_3, z_3), \quad \text{Eqn. 5}$$

and using a straight line approximation for the two line segments that form the cut line, the length of the curved cut line can be estimated as:

$$d_{12} + d_{23} = (x_2-x_1)^2 + (y_2-y_1)^2 + (z_2-z_1)^2 + (x_3-x_2)^2 + (y_3-y_2)^2 + (z_3-z_2)^2. \quad \text{Eqn. 6}$$

Note that while the illustrated curved-line measurement above uses a single intermediate measurement point 605 along the curved-line, one or more additional intermediate measurement points can be added along the same curved-line to increase the overall measurement precision. When more intermediate points are recorded than just point 605, the length of the curved line can be similarly approximated by summing up all of the determined straight-line segments by length measurement subsystem 300 that form the curved line to achieve a higher precision.

In some embodiments, the disclosed length measurement subsystem 300 can be used to estimate a volume of gastric pouch 602. To estimate the volume of gastric pouch 602 (assuming the pouch is full), two parameters, a length $d_2$ and a breadth $d_1$ of gastric pouch 602 need to be determined, which are shown in FIG. 6. Because of the similarity to the geometry of ovoids, the volume of the egg-shaped pouch 602 can be estimated based on the formula of ovoids as:

$$V = k_v d_1 d_2^2, \quad \text{Eqn. 7}$$

wherein $k_v \approx 0.52$ for the geometry of chicken eggs. Note that breadth $d_1$ can be easily calculated as the straight-line distance between point 604 and point 606:

$$d_1 = \sqrt{(x_3-x_1)^2 + (y_3-y_1)^2 + (z_3-z_1)^2}. \quad \text{Eqn. 8}$$

Furthermore, we can derive length $d_2$ as the distance from a point 608 on the pouch 602 to the bottom plane of pouch 602 specified by the three points 604-606. Note that the positions of point 608, which is marked by the tool-tip of a second surgical tool B, can be determined using the disclosed tool-tip position derivation technique by triggering a position measurement with a double-grip on a corresponding UID controlling tool B. Assuming the derived position vector of point 608 is:

$$P_4 = (x_4, y_4, z_4), \quad \text{Eqn. 9}$$

we can calculate pouch length $d_2$ as:

$$d_2 = \frac{|P_4 \cdot N|}{\|N\|}, \quad \text{Eqn. 10}$$

wherein $\vec{N} = \overrightarrow{(P_2-P_1)} \times \overrightarrow{(P_3-P_1)}$ is the normal vector of the bottom plane, i.e., the cross-product of two vectors $\overrightarrow{(P_2-P_1)}$ and $\overrightarrow{(P_3-P_1)}$, which are two non-parallel vectors in the bottom plane. In case that $\vec{N} = 0$ (i.e., points 604-606 form a straight line), then $d_2$ is reduced to the distance between point 608 and the straight line passing through points 604-606, which can be calculated by a normalized dot product of $P_4$ and $\overrightarrow{(P_2-P_1)}$.

Similarly, the disclosed length measurement systems and techniques can be applied to the vaginal dissection procedure mentioned in the background section to measure a section of vaginal length using either the disclosed single-tool measurement technique or the disclosed two-tool measurement technique without having to know the tool geometry.

Figure 7:
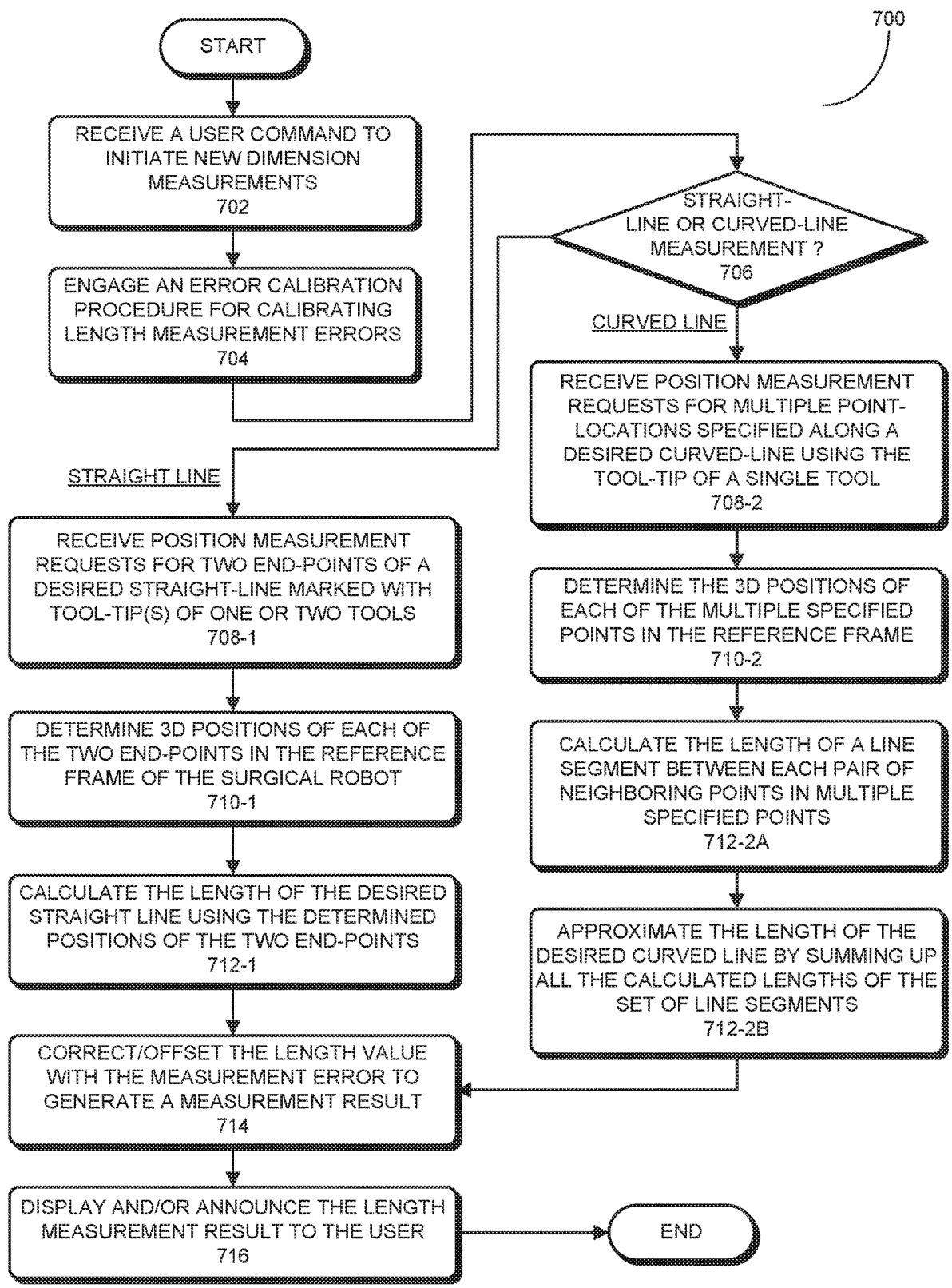
FIG. 7 presents a flowchart illustrating an exemplary process for performing real-time dimension measurements on a tissue/organ using surgical tools of the robotic surgical system in accordance with some embodiments described herein.

FIG. 7 presents a flowchart illustrating an exemplary process 700 for performing real-time dimension measurements on a tissue/organ using one or more engaged surgical tools of a robotic surgical system in accordance with some embodiments described herein. In one or more embodiments, one or more of the steps in FIG. 7 may be omitted, repeated, and/or performed in a different order. Accordingly, the specific arrangement of steps shown in FIG. 7 should not be construed as limiting the scope of the technique.

Process 700 may begin by receiving a user command from a user of the robotic surgical system (e.g., robotic surgical system 100) to initiate new dimension measurements (step 702). In some embodiments, the user of the robotic surgical system such as a surgeon performing a surgical procedure/teleoperation on the robotic surgical system (or the "surgical robot") can initiate new dimension measurements by issuing a voice command or a voice cue. For example, a voice command can include the user calling out "hey, Verby!" followed by "Please take a measurement." Alternatively, the user command can include a hand gesture made by the user (e.g., by waving one or both hands), which can be translated into a command signal by the motion sensors of one or both UIDs of the surgical robot. In some embodiments, a hand gesture command can also be captured by a camera of the surgical robot and recognized through image processing. Moreover, the user command to start new dimension measurements can simply be a pinch on one of the UIDs. Note that all of the above forms of user command can be generated by a surgeon/user without clutching out or disengaging the surgical robot. As more examples, the user can also step on one or more foot controls/pedals of the surgical robot to initiate the new dimension measurements, without clutching out the surgical robot. In yet more examples, the user can simultaneously pinch on the UID and step on the foot pedal to initiate new dimension measurements.

Next, process 700 engages an error calibration procedure for calibrating length measurement errors associated with the disclosed tool-tip position measurements (step 704). During the subsequent error calibration procedure in process 700, multiple calibration measurements can be taken of a reference length of a surgical tool visible in the user display 138. Note that depending on the subsequent length measurement mode, these multiple calibration measurements can be performed with either a single surgical tool or two surgical tools using the disclosed tool-tip-based length measurement techniques. The error calibration procedure can then determine a mean error MAE of the multiple calibration measurements by comparing the multiple length measurement values using the disclosed length measurement techniques against the reference length.

After the error calibration procedure, process 700 next determines whether a straight-line measurement or a curved-line measurement is to be performed (step 706). In some embodiments, process 700 can automatically determine whether to measure a straight-line distance or a curved-line length based on analyzing the received user command in step 702, which can contain additional instructions for specifying which type of measurement (i.e., straight-line or curved-line) to be performed. Alternatively, process 700 can receive another user command specifying whether a straight-line measurement or a curved-line measurement is to be performed. For example, after performing the error calibration procedure, the user can issue a second command as a direct voice command (e.g., "Enter straight line mode!" or "Enter curved line mode!"). The second command can also be one of two predefined hand gestures which can be translated by the surgical robot as one of the two measurement options. Based on the determination at step 706, process 700 enters either the straight-line measurement mode (i.e., the left branch in process 700) or the curved-line measurement mode (i.e., the right branch in process 700).

More specifically, if entering the straight-line measurement mode, process 700 subsequently receives tool-tip position measurement requests for two end-points of a desired straight-line marked with the tool-tip(s) of one or two surgical tools (step 708-1). As described above, the disclosed length measurement subsystem 300 provides the user the options of using either a single surgical tool to specify the locations of the two end-points of the desired straight-line or using two surgical tools to simultaneously specify the locations of the two end-points of the desired straight-line. Moreover, for each specified location, the user can issue a measurement request/command via a UID, a foot pedal, or a combination of both. For example, the user can issue a measurement request by double-pinching a UID or double-tapping a foot pedal. Next, process 700 determines the 3D positions of each of the two end-points in the reference frame of the surgical robot (step 710-1). In some embodiments, process 700 can use the above-described tool-tip position derivation techniques to transform the collected kinematic data for a joint of the surgical tool used in the length measurement into the positions of the tool-tip of the surgical tool at the two specified end-points. Processing 700 subsequently calculates the length of the desired straight-line using the determined 3D positions of the two end-points (step 712-1).

Alternatively, if entering the curved-line measurement mode, process 700 subsequently receives tool-tip position measurement requests for multiple point-locations specified along a desired curved-line using the tool-tip of a single surgical tool (step 708-2). As described above, the disclosed length measurement subsystem 300 allows the user to use the tool-tip of a single surgical tool to swipe along an intended trajectory between a starting point and an end point to trace out the desired curved-line, and as the user is guiding the tool-tip along the trajectory, multiple point-locations (or simply "points") along the trajectory can be specified by issuing multiple measurement requests/commands at these multiple point-locations.

Next, process 700 determines the 3D positions of each of the multiple specified points in the reference frame of the surgical robot (step 710-2). In some embodiments, process 700 can use the above-described tool-tip position derivation techniques to transform the collected kinematic data for a joint of the surgical tool used in the length measurement into the positions of the tool-tip of the surgical tool at each of the multiple specified points. Next, processing 700 calculates the length of a line segment between each pair of neighboring points in multiple specified points (step 712-2A). Processing 700 subsequently approximates the length of the desired curved-line by summing up all of the calculated lengths of the set of line segments in the curved-line (step 712-2B). It can be appreciated that for the curved-line measurement, when more intermediate points along the curved-line are specified and their 3D positions are obtained, the corresponding length measurement result for the same curved-line generally becomes more accurate.

After a length value for a straight-line or a curved-line is generated either from step 712-1 or from step 712-2B, process 700 next correct/offset the length value with the determined measurement error to generate a length measurement result (step 714). Finally, process 700 displays and/or announces the length measurement result for the straight-line or the curved-line to the user as real-time feedback (step 716).

Note that compared to existing length measurement techniques, the disclosed length measurement techniques based on robotic kinetic data can achieve various improvements and benefits. For example, the disclosed length measurement techniques utilize one or more surgical tools which are already inside the patient's body to specify a number of measurement locations on a tissue or an organ without having to move a physical ruler in and out of patient's body. These measurement techniques can utilize available kinematic data at robotic arm joints and tool joints to derive the positions of the tool-tip(s) needed for the length measurements. Moreover, instead of limiting to straight-line measurements, the disclosed length measurement techniques can measure an arbitrarily shaped curved-line or even a circumference, which is not possible with a paper ruler.

Robotic-Assisted Bowel Measurement

During a RYGB surgery, to measure a bowel length with the running the bowel technique, the surgeon usually grasps and pulls the small bowel alternatively with two bipolar forceps: i.e., the left and the right bipolar forceps, while estimating the length of each pull. For example, the surgeon may begin by grasping the bowel with the left forceps, pull the bowel up (in a relative "up" direction in the endoscope video shown on the screen) and hold momentarily. The surgeon next uses the right forceps to grasp the bowel at a location shown near the bottom of the screen, and then releases the left forceps. Next, the surgeon may again pull up and hold the bowel with the right forceps, and then grasp the bowel from the bottom again with the left forceps, so that the right forceps can be released.

In some embodiments, when the left and the right forceps are attached to robotic arms 112 in robotic surgical system 100, each pair of forceps can be controlled by a corresponding UID 136, and a pressure/grip force applied by the pair of grippers of the forceps corresponds to a grip force (i.e., a pressure) applied on the corresponding UID 136. Hence, each time a pair of forceps grasps the bowel, a peak pressure is also applied on the corresponding UID 136, and the corresponding pressure value can be registered as an input data point in a log file of the UID grip force. Conversely, each time the same pair of forceps releases the bowel, a minimum pressure is applied on the corresponding UID 136, and the corresponding pressure value can be registered as another input data point in a log file of the UID grip force. As a result, the alternative grasping and pulling actions by the two pairs of forceps can be identified from the log files of the measured UID grip force.

Figure 8:
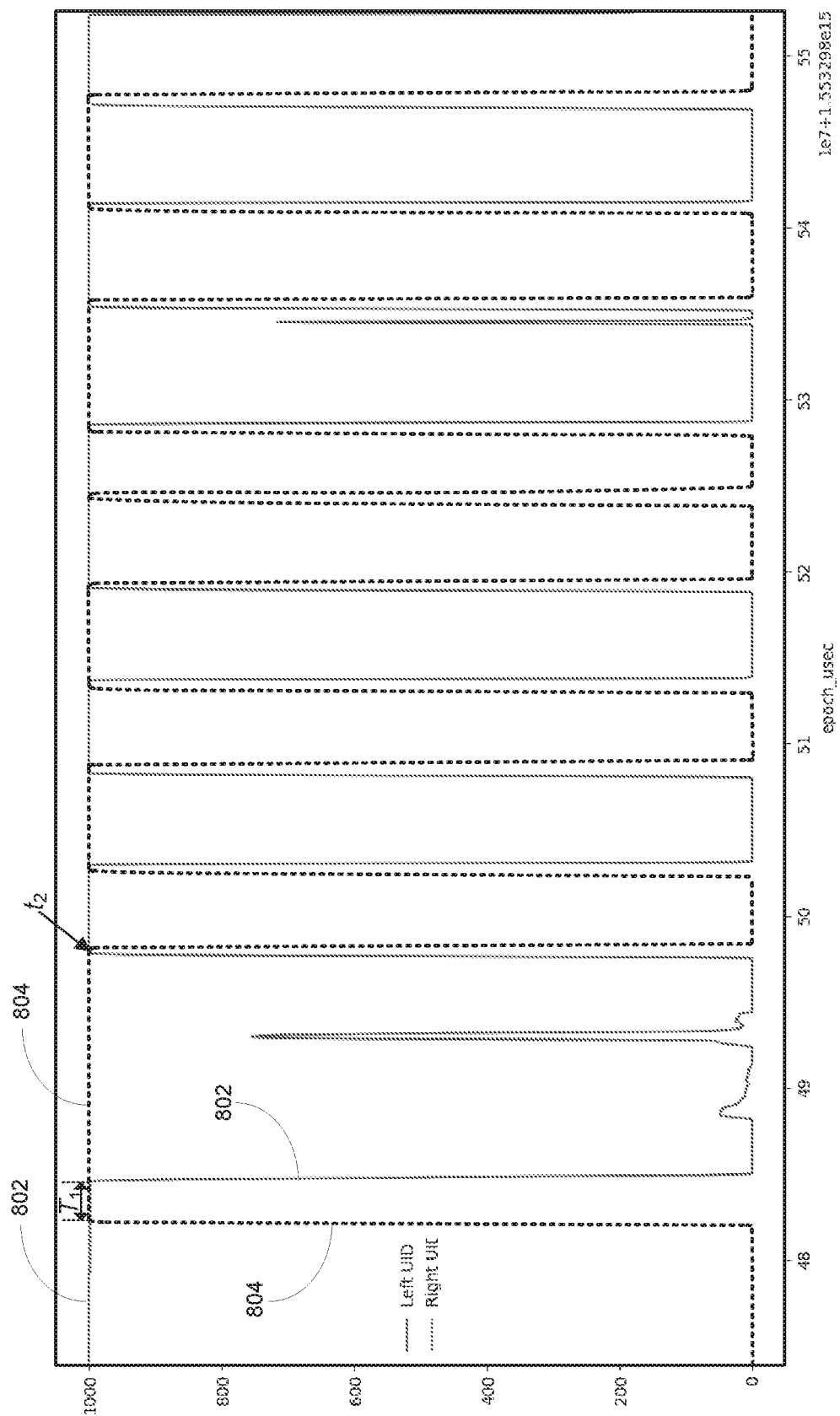
FIG. 8 illustrated a data plot of UID grip force (i.e., pressure) as a function of time during an experiment when two pairs of forceps to alternatively grasping and pulling on a bowel in accordance with some embodiments described herein.

FIG. 8 illustrated a data plot 800 of UID grip force (i.e., pressure) as a function of time during an experiment when two pairs of forceps alternatively grasping and pulling on a bowel in accordance with some embodiments described herein. More specifically, the solid data curve/pattern 802 in plot 800 corresponds to the left UID for controlling the left pair of forceps (or "the left forceps") and the dashed data curve/pattern 804 in plot 800 corresponds to the right UID for controlling the right pair of forceps (or "the right forceps"). As can be seen in FIG. 8, at the beginning of the experiment, the left pair of forceps is grasping the bowel at the maximum grip force/pressure by applying a maximum grip force on the left UID, while the right pair of forceps ramps up the grip force through the right UID after epoch timestamp 48e7+1.553298e15 c. The pressure values from both UIDs then overlap at the max pressure value (i.e., "1000") for a short period of time denoted as "$T_1$," corresponding to the moment during which the left pair of forceps is stilling holding onto the bowel but about to be released while the right pair of forceps is grasping the bowel and about to pull.

Subsequently, the left pair of forceps is released by releasing the left UID, causing the recorded UID pressure values to drop to a minimum value or zero; while the right pair of forceps is grasping at the maximum grip force by applying a maximum grip force on the right UID. We refer to this time period from when the grip force of the one UID (e.g., the right UID) begins to rise from the minimum value until when the grip force of the other UID (e.g., the left UID) begins to fall from the maximum value as a grip force switching cycle. As can be seen in FIG. 8, the next switching cycle occurs just before epoch time 50e7+1.553298e15 pec, when the pressure value of the left UID switches from a minimum value to the maximum value, while the pressure value of the right UID switches from the maximum value to the minimum value.

In some embodiments, to compute the length of a section of the bowel while performing "running the bowel," the distance between the two tool-tips of the two pairs of forceps right before the moment of the second grip force "switching" in a grip force switching cycle, i.e., at the end of time period $T_1$ can be measured and used as the section length, because at this moment both pairs of forceps are grasping the bowel at the maximum pressure. As described above, kinematic data including the positions and orientations of a tool joint at the distal end of each pair of forceps can be collected. For example, the positions and orientations of a wrist joint connecting the graspers to the shaft of each pair of forceps can be collected. Next, the 3D positions of the two tool-tips of the two pairs of forceps can be derived based on the corresponding joint positions and orientations using the above-described tool-tip position derivation techniques, e.g., using tool-tip position derivation module 312. In some embodiments however, 3D positions of the tool-tips may be directed estimated rather than being derived. For example, if the distance between the wrist joint where kinematic data can be collected and a corresponding tool-tip is sufficiently small, it can be a sufficiently good approximation to use the 3D positions of the wrist joint as the positions of the corresponding tool-tip.

Note that taking the length measurement of each section of the bowel can be automatically performed instead of triggered by user generated commands. More specifically, the positions of both tool-tips of the two pairs of forceps can be constantly calculated and/or recorded during the time period when both UID grip forces are at their maximum value, such as during time period $T_1$. In other words, this is the brief moment when both pairs of forceps are grasping onto the bowel. To further improve measurement accuracy, UID grip force readings can be time-synchronized with the corresponding tool-tip position calculations and/or readings in the time window when both UID grip forces are at the maximum values. In some embodiments, when the end of a switching cycle is detected based on the UID pressure values (e.g., at the end of time period $T_1$ when the left UID pressure begins to fall), the last calculated and/or recorded positions of both tool-tips right before the end of the switching cycle can be used to compute the distance between the two tool-tips, and the computed distance can be used to represent the length of a corresponding section of the bowel.

Note that the above-described process for measuring one section of the bowel length can be repeated during the entire running the bowel procedure to generate an accumulated length of bowel. In some embodiments, as the bowel length is being accumulated, the disclosed bowel length measurement technique can automatically display and/or announce the dynamically-updated measurement result in real-time on the screen as real-time feedback until the running the bowel procedure is complete.

In some embodiments, instead of using the distance between two pairs of forceps when they are both grasping onto the bowel at holding steady, the travel distance of either the left or the right pair of forceps while grasping onto the bowel can be measured to represent the length of a section of the bowel being pulled. In these embodiments, the positions of a single tool-tip of a single pair of forceps at two different time stamps can be calculated and/or recorded. For example, one position calculation or direct position reading can take place at a "switching-in" moment, i.e., the moment when a given pair of forceps just grasps onto bowel but before pulling on it; and the other position calculation or direct position reading can take place at a "switching-out" moment, i.e., the moment when the same pair of forceps is about to be released. Note that this switching-in moment can correspond to the beginning of time period $T_1$ in FIG. 8, while the corresponding switching-out moment can correspond to the end of next switching cycle, e.g., at timestamp $t_2$ shown in FIG. 8. Similarly, the above-described process for measuring one section of the bowel can be repeated during the entire running the bowel procedure to generate an accumulated length of bowel. In some embodiments, as the bowel length is being accumulated, the disclosed bowel length measurement technique can automatically display and/or announce the dynamically-change measurement result in real-time on the screen as real-time feedback to the surgeon until the running the bowel procedure is complete.

Figure 9:
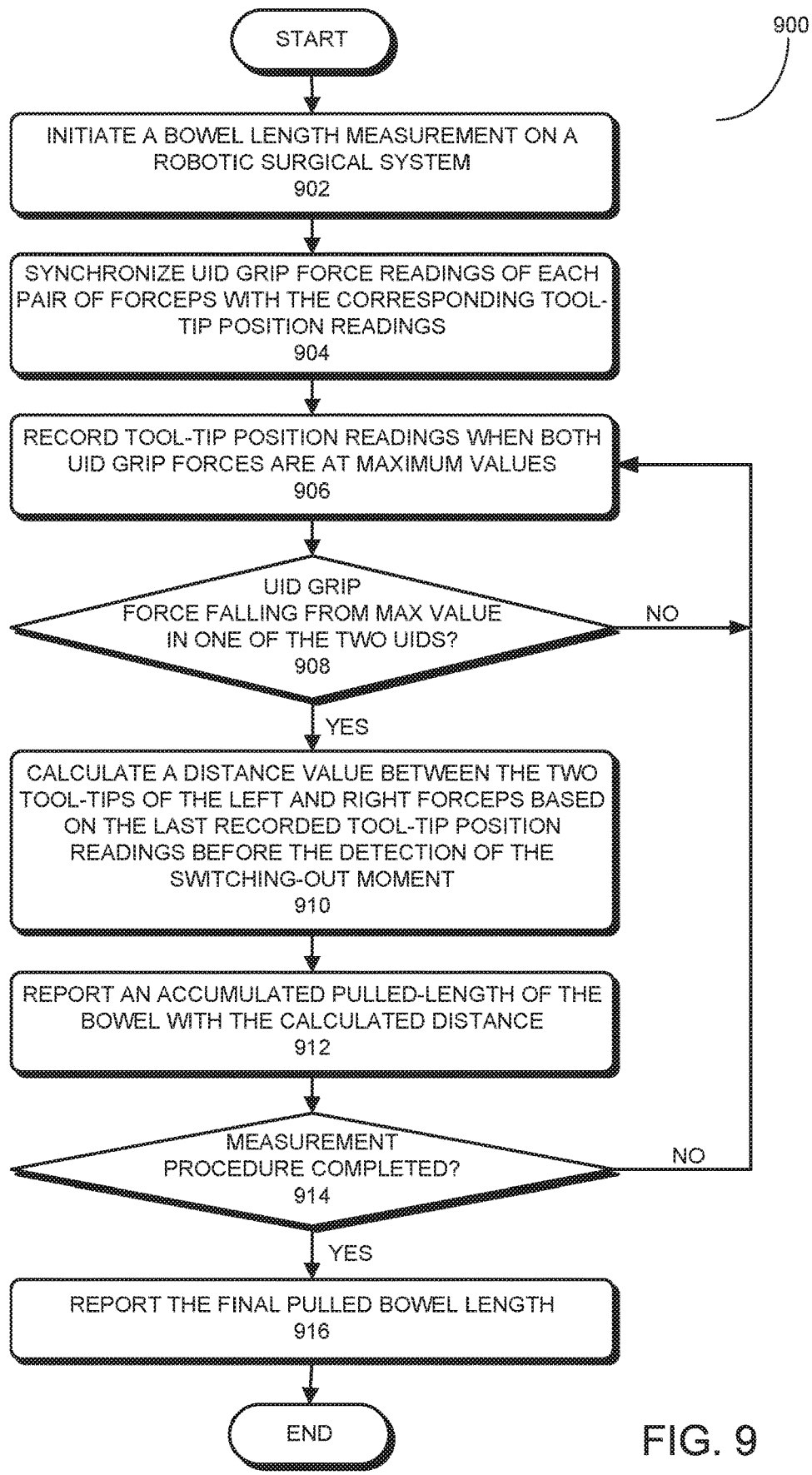
FIG. 9 presents a flowchart illustrating an exemplary process for performing a robotic-assisted bowel-length measurement based on measuring distances between the two tool-tips of two pairs of forceps in accordance with some embodiments described herein

FIG. 9 presents a flowchart illustrating an exemplary process 900 for performing a robotic-assisted bowel-length measurement based on measuring distances between two tool-tips of two pairs of forceps in accordance with some embodiments described herein. In one or more embodiments, one or more of the steps in FIG. 9 may be omitted, repeated, and/or performed in a different order. Accordingly, the specific arrangement of steps shown in FIG. 9 should not be construed as limiting the scope of the technique.

Process 900 may begin by initiating a bowel length measurement on a robotic surgical system (e.g., robotic surgical system 100) (step 902). In some embodiments, a new bowel length measurement can be automatically initiated by the robotic surgical system. For example, the system can be configured to actively monitor the types of surgical tools being swapped into and out of the patient's body and begin a new measurement when both the left and right forceps are brought into the patient's body. In some embodiments, the system can detect the presents of the left and right forceps based on processing surgical video data 306. For example, the system can employ a machine-learning or computer-vision technique to detect various surgical tools captured in surgical video data 306.

Alternatively, a new bowel length measurement can be initiated by the user of the system such as a surgeon. In these embodiments, the user can initiate a new length measurement by providing a voice command or a voice cue. For example, a voice cue can include the user calling out "Hey Verb, begin measure!" The user can also initiate a new length measurement by inputting other forms of commands into the system, such as pinching on the UID, stepping on the foot pedal, or a combination of both. In some embodiments, process 900 can also be ended in similar manners, e.g., based on monitoring and identifying certain tool events in the captured surgical video images, or based on receiving direct commands from the user/surgeon to end the measurement.

Once the new bowel length measurement is initiated, process 900 then synchronizes UID grip force readings of each pair of forceps with the corresponding tool tip position readings (step 904). As described above, the hand-over-hand-pulling pattern during the bowel length measurement is reflected in the UID grip force values of each pairs of forceps as high-low cycles, and the time-window to capture or record the tool-tip positions when both UID grip forces are at the maximum values can be very short. Hence, by time-synchronizing UID grip force readings with the corresponding tool-tip position readings, the system is configured to measure and record the tool-tip positions at the exact moments when tool-tip positions are considered optimal for taking the position measurements.

After data readout synchronizing, process 900 records tool-tip position readings when both UID grip forces are at maximum values (i.e., when both the left and right forceps are grasping onto the bowel) (step 906). Note that process 900 can use the disclosed tool-tip position derivation module 312 to derive the tool-tip position readings for each placement of the two tool-tips of the left and right forceps. While recording tool-tip positions, process 900 detects if the UID grip force of one of the two UIDs begins to fall from the maximum value (i.e., the end of a switching cycle) (step 908). Note that step 908 essentially detects a "switching-out" moment of a pair of forceps, i.e., the moment when the pair of forceps is about to be released.

If no switching-out moment is detected, process 900 returns to step 906 and continues recording tool-tip position readings. Otherwise, when a switching-out moment is detected at step 908, i.e., when the UID grip force of one of the two UIDs begins to fall from the maximum value, process 900 calculates a distance value between the two tool-tips of the left and right forceps based on the last recorded tool-tip position readings before the detection of the switching-out moment (step 910). Process 900 then reports an accumulated pulled-length of the bowel after updating the total pulled-length with the newly calculated distance (step 912). Next, process 900 further determines if the running the bowel procedure is completed (step 914). If not, process 900 returns to step 906 to begin the measurement for the next pulled section of the bowel. Otherwise, process 900 reports the final pulled-length of the bowel and the process terminates (step 916).

Figure 10:
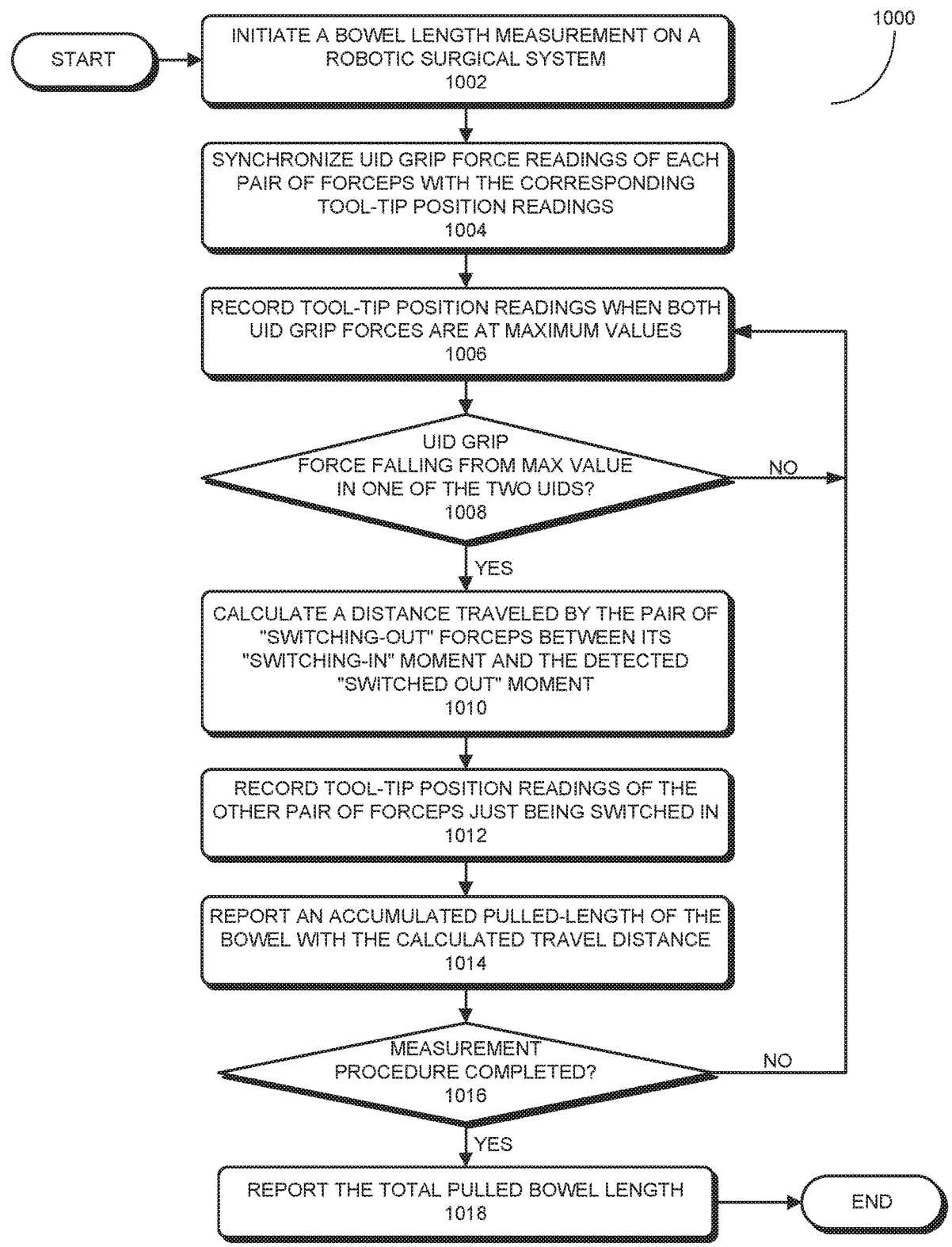
FIG. 10 presents a flowchart illustrating an exemplary process for performing a robotic-assisted bowel-length measurement based on the distance traveled by the two tool-tips of two pairs of forceps in accordance with some embodiments described herein.

FIG. 10 presents a flowchart illustrating an exemplary process 1000 for performing a robotic-assisted bowel-length measurement based on the distance traveled by the two tool-tips of two pairs of forceps in accordance with some embodiments described herein. In one or more embodiments, one or more of the steps in FIG. 10 may be omitted, repeated, and/or performed in a different order. Accordingly, the specific arrangement of steps shown in FIG. 10 should not be construed as limiting the scope of the technique.

Note that steps 1002-1006 of process 1000 are substantially identical to the respective steps 902-906 of process 900, and therefore are not repeated herein. We begin describing process 1000 from step 1008. While recording tool-tip positions, process 1000 detects if the UID grip force of one of the two UIDs begins to fall from the maximum value (i.e., the end of a switching cycle) (step 1008). Note that step 1008 detects a "switching-out" moment of a pair of forceps, i.e., the moment when the pair of forceps is about to be released. If not, process 1000 returns to step 1006 and continues recording tool-tip position readings. Otherwise, when a switching-out moment is detected for a given pair of forceps at step 1008, process 1000 subsequently calculates a distance traveled by the given pair of forceps between its "switching-in" moment in the current switching cycle and the detected "switched out" moment in the same switching cycle (i.e., the time window during which the given pair of forceps was grasping the bowel) (step 1010).

Subsequently, process 1000 records tool-tip position readings of the other pair of forceps which has just been switched in (step 1012). Process 1000 then reports an accumulate d pulled-length of the bowel after updating the total pulled-length with the newly-calculated travel distance (step 1014). Next, process 1000 further determines if the running the bowel procedure is completed (step 1016). If not, process 1000 returns to step 1006 to begin the measurement for the next pulled section of the bowel. Otherwise, process 1000 reports the total pulled-length of the bowel and process 1000 terminates (step 1018).

In some embodiments, the recorded tool-tip position data and/or UID grip force data can also be used for evaluating the performance of a surgeon performing the bowel procedure. For example, an average length of each pull of the bowel can be determined by dividing the total measured bowel length by the number of switching cycles in collected the UID grip force data. Another application of using the above recorded tool data is to determine an efficiency metric, which can be defined as the number of effective/successful grasps of the bowel divided by the total number of attempted grasps. For example, using the UID data in FIG. 8, this efficiency metric can be calculated as follows: for the left UID, the total number of attempted grasps (successful or not) is 8 according to data curve 802, of which 6 are successful grasps (i.e., where actual switching happened. Hence, the left UID has an efficiency metric of ⅞=75%. Similarly, for the right UID and by processing data curve 802, the efficiency metric is ⅚=83.3%.

Figure 11:
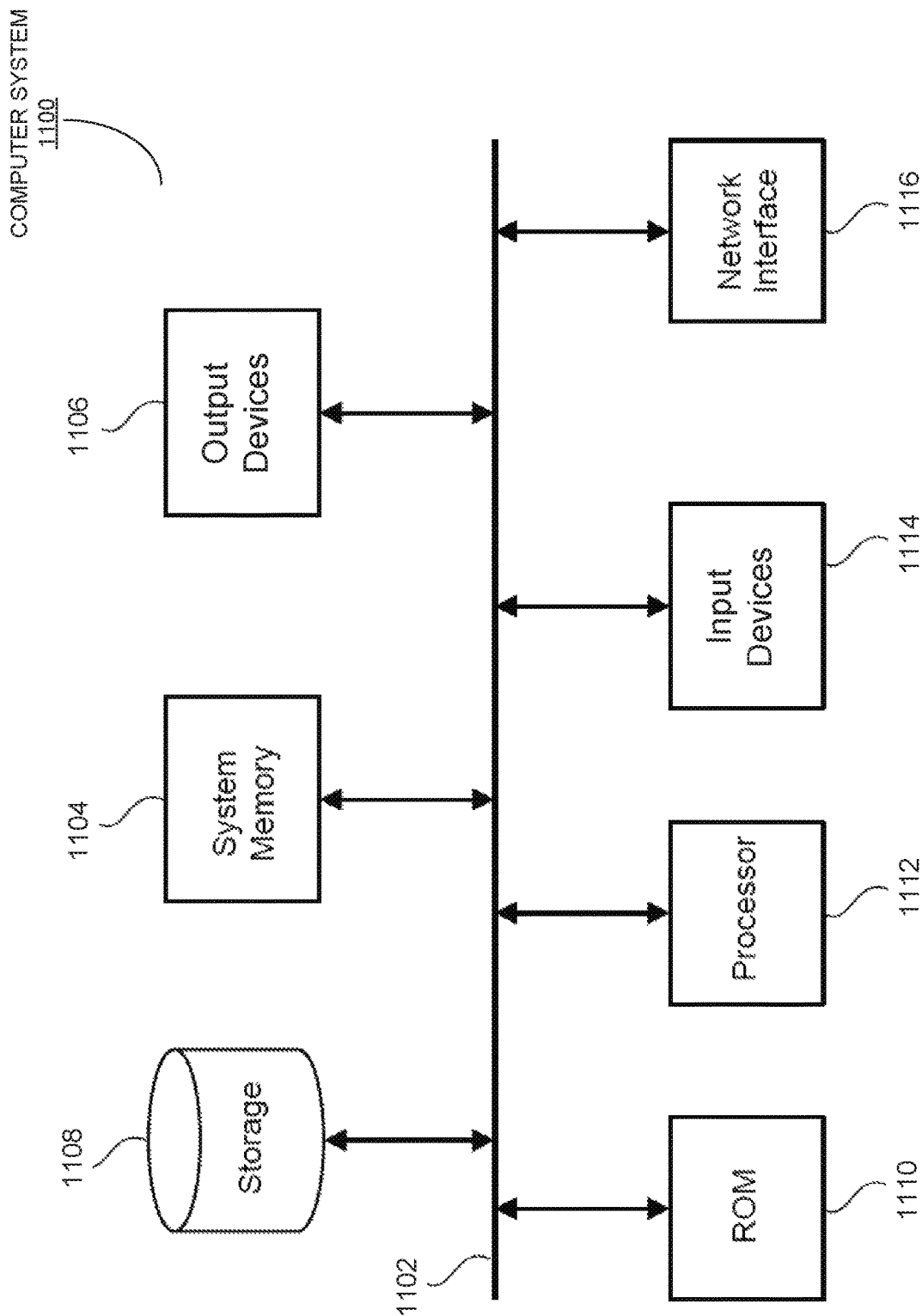
FIG. 11 conceptually illustrates a computer system with which some embodiments of the subject technology can be implemented.

FIG. 11 conceptually illustrates a computer system with which some embodiments of the subject technology can be implemented. Computer system 1100 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 1100 includes a bus 1102, processing unit(s) 1112, a system memory 1104, a read-only memory (ROM) 1110, a permanent storage device 1108, an input device interface 1114, an output device interface 1106, and a network interface 1116. In some embodiments, computer system 1100 is a part of a robotic surgical system.

Bus 1102 collectively represents all system, peripheral, and chipset buses that communicatively connect the numerous internal devices of computer system 1100. For instance, bus 1102 communicatively connects processing unit(s) 1112 with ROM 1110, system memory 1104, and permanent storage device 1108.

From these various memory units, processing unit(s) 1112 retrieves instructions to execute and data to process in order to execute various processes described in this patent disclosure, including the above-described processes of performing various real-time robotic-assisted length measurements of tissues and organs using surgical tools of the robotic surgical system described in conjunction with FIGS. 3-10. The processing unit(s) 1112 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 1112 can be a single processor or a multi-core processor in different implementations.

ROM 1110 stores static data and instructions that are needed by processing unit(s) 1112 and other modules of the computer system. Permanent storage device 1108, on the other hand, is a read-and-write memory device. This device is a non-volatile memory unit that stores instructions and data even when computer system 1100 is off. Some implementations of the subject disclosure use a mass-storage device (such as a magnetic or optical disk and its corresponding disk drive) as permanent storage device 1108.

Other implementations use a removable storage device (such as a floppy disk, flash drive, and its corresponding disk drive) as permanent storage device 1108. Like permanent storage device 1108, system memory 1104 is a read-and-write memory device. However, unlike storage device 1108, system memory 1104 is a volatile read-and-write memory, such as a random access memory. System memory 1104 stores some of the instructions and data that the processor needs at runtime. In some implementations, various processes described in this patent disclosure, including the processes of performing various real-time robotic-assisted length measurements of tissues and organs using surgical tools of the robotic surgical system described in conjunction with FIGS. 3-10, are stored in system memory 1104, permanent storage device 1108, and/or ROM 1110. From these various memory units, processing unit(s) 1112 retrieves instructions to execute and data to process in order to execute the processes of some implementations.

Bus 1102 also connects to input and output device interfaces 1114 and 1106. Input device interface 1114 enables the user to communicate information to and select commands for the computer system. Input devices used with input device interface 1114 include, for example, alphanumeric keyboards and pointing devices (also called "cursor control devices"). Output device interface 1106 enables, for example, the display of images generated by the computer system 1100. Output devices used with output device interface 1106 include, for example, printers and display devices, such as cathode ray tubes (CRT) or liquid crystal displays (LCD). Some implementations include devices such as a touchscreen that functions as both input and output devices.

Finally, as shown in FIG. 11, bus 1102 also couples computer system 1100 to a network (not shown) through a network interface 1116. In this manner, the computer can be a part of a network of computers (such as a local area network ("LAN"), a wide area network ("WAN"), an intranet, or a network of networks, such as the Internet. Any or all components of computer system 1100 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for performing real-time robotic-assisted length measurements within a robotic surgical system, the method comprising:
    after initiating a length measurement during a surgical procedure on a patient, calibrating measurement errors associated with using a tool-tip of a first surgical tool with a known length of a second surgical tool of the robotic surgical system, wherein the first surgical tool is attached to a robotic arm comprising a plurality of arm joints, wherein the measurement errors include an accumulated encoder error associated with a plurality of encoders of the plurality of arm joints;
    obtaining a first set of kinematic data of a wrist joint of the first surgical tool corresponding to placing the tool-tip of the first surgical tool at a first location on an anatomy, wherein the first set of kinematic data are measured relative to a base reference frame;
    obtaining a second set of kinematic data of the wrist joint of the first surgical tool corresponding to placing the tool-tip of the first surgical tool at a second location on the anatomy, wherein the second set of kinematic data are measured relative to the base reference frame;
    transforming the first set of kinematic data into a first position vector of the tool-tip at the first location and the second set of kinematic data into a second position vector of the tool-tip at the second location; and
    computing a first distance between the first position vector and the second position vector as a measured length of a straight line between the first location and the second location on the anatomy.

2. The computer-implemented method of claim 1, wherein prior to obtaining the first set and the second set of kinematic data and prior to calibrating the measurement errors, the method further comprises receiving a first user command to initiate the length measurement on the anatomy via a user interface device (UID) of the robotic surgical system.

3. The computer-implemented method of claim 2, wherein after initiating the length measurement, the method further comprises:
    receiving a second user command indicative of whether the length measurement is a straight-line measurement or a curved-lined measurement; and
    entering either a straight-line measurement mode or a curved-line measurement mode after processing the second user command.

4. The computer-implemented method of claim 1, wherein obtaining the first set or the second set of kinematic data of the wrist joint of the first surgical tool includes:
    retrieving, from a data log of the robotic surgical system, a position vector corresponding to a center point of the wrist joint; and
    retrieving, from the data log, a rotation vector corresponding to an orientation of an end effector of the first surgical tool connected to the wrist joint, wherein the end effector is positioned between the wrist joint and the tool-tip.

5. The computer-implemented method of claim 4, wherein transforming the first set or the second set of kinematic data into the first position vector or the second position vector of the first location or the second location includes:
    computing a rotational displacement of the tool-tip with respect to the center point of the wrist joint based at least on the corresponding rotation vector and a length of the end effector; and
    obtaining the first position vector or the second position vector of the first location or the second location by combining the first position vector or the second position vector of the center point of the wrist joint with the corresponding rotational displacement.

6. The computer-implemented method of claim 1, wherein the plurality of arm joints includes a first arm joint and a last arm joint, and wherein obtaining the first set or the second set of kinematic data of the wrist joint includes:
    for each arm joint in the plurality of arm joints, obtaining a set of kinematic data generated by an encoder of the arm joint, wherein the set of kinematic data are measured relative to a reference frame of the arm joint;
    performing a series of forward transformations from the first arm joint to the last arm joint using the sets of kinematic data associated with the plurality of arm joints, wherein each forward transformation in the series of forward transformations transforms the corresponding set of kinematic data at the corresponding arm joint into a transformed set of kinematic data for the corresponding arm joint relative to the base frame; and
    performing a final forward transformation which transforms the transformed set of kinematic data at the final arm joint into the first set or the second set of kinematic data of the wrist joint of the first surgical tool in the base frame.

7. The computer-implemented method of claim 1, wherein calibrating the measurement errors with the known length of the second surgical tool includes:
    taking multiple length measurements of the known length using the tool-tip of the first surgical tool to obtain a set of measurement values of the known length; and
    comparing the set of measurement values against the known length to obtain a mean error of the set of measurement values.

8. The computer-implemented method of claim 7, wherein taking a length measurement of the known length using the tool-tip of the first surgical tool includes:
   obtaining a third position vector of the tool-tip at a first end-point of the known length on the second surgical tool;
   obtaining a fourth position vector of the tool-tip at a second end-point of the known length on the second surgical tool; and
   generating a measurement value of the known length as the distance between the third position vector and the fourth position vector.

9. The computer-implemented method of claim 1, wherein the method further comprises using the calibrated measurement errors to offset the measured length of the straight line to improve a measurement accuracy of using the tool-tip of the first surgical tool for length measurements.

10. The computer-implemented method of claim 1, wherein the method further comprises:
   obtaining a third set of kinematic data of the wrist joint of the first surgical tool corresponding to placing the tool-tip of the first surgical tool at a third location on the anatomy, wherein the third set of kinematic data are measured relative to the base reference frame;
   transforming the third set of kinematic data into a third position vector of the tool-tip at the third location;
   computing a second distance between the second position vector and the third position vector as a measured length of a straight line between the second location and the third location on the anatomy; and
   outputting a sum of the first distance and the first distance as an approximated length of a curved line specified by the first, the second and the third locations.

11. A processor of a robotic surgical system, the processor configured to:
   after initiating a length measurement during a surgical procedure on a patient, calibrate measurement errors associated with using a tool-tip of a first surgical tool with a known length of a second surgical tool of the robotic surgical system, wherein the first surgical tool is attached to a robotic arm comprising a plurality of arm joints, wherein the measurement errors include an accumulated encoder error associated with a plurality of encoders of the plurality of arm joints;
   obtain a first set of kinematic data of a wrist joint of the first surgical tool corresponding to placing the tool-tip of the first surgical tool at a first location on an anatomy, wherein the first set of kinematic data are measured relative to a base reference frame;
   obtain a second set of kinematic data of the wrist joint of the first surgical tool corresponding to placing the tool-tip of the first surgical tool at a second location on the anatomy, wherein the second set of kinematic data are measured relative to the base reference frame;
   transform the first set of kinematic data into a first position vector of the tool-tip at the first location and the second set of kinematic data into a second position vector of the tool-tip at the second location; and
   compute a first distance between the first position vector and the second position vector as a measured length of a straight line between the first location and the second location on the anatomy.

12. The processor of claim 11, wherein the processor is configured to receive, prior to obtaining the first set and the second set of kinematic data and prior to calibrating the measurement errors, a first user command to initiate the length measurement on the anatomy via a user interface device (UID) of the robotic surgical system.

13. The processor of claim 12, wherein after initiating the length measurement, the processor is configured to:
   receive a second user command indicative of whether the length measurement is a straight-line measurement or a curved-lined measurement; and
   enter either a straight-line measurement mode or a curved-line measurement mode after processing the second user command.

14. The processor of claim 11, wherein obtaining the first set or the second set of kinematic data of the wrist joint of the first surgical tool includes:
   retrieving, from a data log of the robotic surgical system, a position vector corresponding to a center point of the wrist joint; and
   retrieving, from the data log, a rotation vector corresponding to an orientation of an end effector of the first surgical tool connected to the wrist joint, wherein the end effector is positioned between the wrist joint and the tool-tip.

15. The processor of claim 11, wherein transforming the first set or the second set of kinematic data into the first position vector or the second position vector of the first location or the second location includes:
   computing a rotational displacement of the tool-tip with respect to a center point of the wrist joint based at least on a rotation vector and a length of an end effector of the surgical tool; and
   obtaining the first position vector or the second position vector of the first location or the second location by combining the first position vector or the second position vector of the center point of the wrist joint with the rotational displacement.

16. The processor of claim 11, wherein the plurality of arm joints, including a first arm joint and a last arm joint, and wherein obtaining the first set or the second set of kinematic data of the wrist joint includes:
   for each arm joint in the plurality of arm joints, obtaining a set of kinematic data generated by an encoder of the arm joint, wherein the set of kinematic data are measured relative to a reference frame of the arm joint;
   performing a series of forward transformations from the first arm joint to the last arm joint using the sets of kinematic data associated with the plurality of arm joints, wherein each forward transformation in the series of forward transformations transforms the corresponding set of kinematic data at the corresponding arm joint into a transformed set of kinematic data for the corresponding arm joint relative to the base frame; and
   performing a final forward transformation which transforms the transformed set of kinematic data at the final arm joint into the first set or the second set of kinematic data of the wrist joint of the first surgical tool in the base frame.

17. A non-transitory machine-readable medium having instructions which when executed by at least one processor of a robotic surgical system causes the robotic surgical system to:
   after initiating a length measurement during a surgical procedure on a patient, calibrate measurement errors associated with using a tool-tip of a first surgical tool with a known length of a second surgical tool of the robotic surgical system, wherein the first surgical tool is attached to a robotic arm comprising a plurality of arm joints, wherein the measurement errors include an accumulated encoder error associated with a plurality of encoders of the plurality of arm joints;

obtain a first set of kinematic data of a wrist joint of the first surgical tool corresponding to placing the tool-tip of the first surgical tool at a first location on an anatomy, wherein the first set of kinematic data are measured relative to a base reference frame;

obtain a second set of kinematic data of the wrist joint of the first surgical tool corresponding to placing the tool-tip of the first surgical tool at a second location on the anatomy, wherein the second set of kinematic data are measured relative to the base reference frame;

transform the first set of kinematic data into a first position vector of the tool-tip at the first location and the second set of kinematic data into a second position vector of the tool-tip at the second location; and compute a first distance between the first position vector and the second position vector as a measured length of a straight line between the first location and the second location on the anatomy.

18. The non-transitory machine-readable medium of claim 17, wherein the non-transitory machine-readable medium comprises further instructions to receive, prior to obtaining the first set and the second set of kinematic data and prior to calibrating the measurement errors, a first user command to initiate the length measurement on the anatomy via a user interface device (UID) of the robotic surgical system.

* * * * *